(12) United States Patent
Dorr et al.

(10) Patent No.: US 8,088,169 B2
(45) Date of Patent: Jan. 3, 2012

(54) PROSTHETIC HIP IMPLANTS

(76) Inventors: Lawrence D. Dorr, La Canada, CA (US); Aaron Rosenberg, Deerfield, IL (US); Wayne G. Paprosky, Winfield, IL (US)

( * ) Notice: Subject to any disclaimer, the term of this patent is extended or adjusted under 35 U.S.C. 154(b) by 0 days.

(21) Appl. No.: 12/776,571

(22) Filed: May 10, 2010

(65) Prior Publication Data

US 2010/0222893 A1    Sep. 2, 2010

Related U.S. Application Data

(63) Continuation of application No. 11/687,862, filed on Mar. 19, 2007, now abandoned.

(60) Provisional application No. 60/783,880, filed on Mar. 20, 2006.

(51) Int. Cl.
*A61F 2/32* (2006.01)

(52) U.S. Cl. ............... 623/23.59; 623/23.32; 623/23.46; 623/23.55

(58) Field of Classification Search ............... 623/23.32, 623/23.46, 23.55, 23.59
See application file for complete search history.

(56) References Cited

U.S. PATENT DOCUMENTS

| | | | |
|---|---|---|---|
| 3,808,606 A * | 5/1974 | Tronzo ........................ | 428/613 |
| 4,141,088 A | 2/1979 | Treace et al. | |
| 4,447,915 A | 5/1984 | Weber | |
| 4,546,501 A | 10/1985 | Gustilo et al. | |
| 4,650,489 A | 3/1987 | Thompson | |
| 4,792,339 A | 12/1988 | Tepic | |
| 4,813,963 A | 3/1989 | Hori et al. | |
| 4,895,573 A | 1/1990 | Koeneman et al. | |
| 5,007,931 A | 4/1991 | Smith | |
| 5,156,627 A | 10/1992 | Amstutz et al. | |
| 5,176,712 A * | 1/1993 | Homsy ........................ | 623/23.36 |
| 5,236,457 A | 8/1993 | Devanathan | |
| 5,246,461 A * | 9/1993 | Tepic ........................ | 623/23.32 |
| 5,443,512 A | 8/1995 | Parr et al. | |
| 5,480,451 A | 1/1996 | Grundei et al. | |
| 5,593,451 A | 1/1997 | Averill | |
| 5,653,764 A | 8/1997 | Murphy | |
| 5,702,487 A | 12/1997 | Averill | |
| 5,863,295 A | 1/1999 | Averill | |

(Continued)

FOREIGN PATENT DOCUMENTS

CH            507704         5/1971

(Continued)

OTHER PUBLICATIONS

Webpage—Zimmer Epoch® Hip Prosthesis www.zimmer.com, 2007 Zimmer, Inc.—accessed Mar. 13, 2008.
Brochure—Zimmer Epoch® Hip Prosthesis 97-4075-01 Rev, Zimmer, Inc. 2002, 8 pages.

(Continued)

*Primary Examiner* — Bruce E Snow
*Assistant Examiner* — Melissa Hoban
(74) *Attorney, Agent, or Firm* — Baker & Daniels LLP

(57) ABSTRACT

Prosthetic hip stems and acetabular cups for use in prosthetic hip joints. The hip stem may include a core having a stem portion and a neck portion, a polymer matrix layer substantially covering the stem portion of the core, and a porous metal layer substantially covering the polymer matrix layer. The polymer matrix layer connects the core and the porous metal layer and provides a stiffness for the hip stem which more closely mimics the stiffness of bone than do known hip stems. The hip stems and acetabular cups additionally include a number of improvements adapted for more optimized results with certain types of patient anatomy, such as the anatomy of female patients, for example.

21 Claims, 22 Drawing Sheets

U.S. PATENT DOCUMENTS

| | | | |
|---|---|---|---|
| 6,126,691 | A | 10/2000 | Kasra et al. |
| 6,136,035 | A | 10/2000 | Lob et al. |
| 6,190,417 | B1 | 2/2001 | Itoman et al. |
| 6,355,069 | B1 | 3/2002 | DeCarlo, Jr. et al. |
| 6,383,225 | B2 | 5/2002 | Masini |
| 6,395,327 | B1 | 5/2002 | Shetty |
| 6,514,288 | B2 | 2/2003 | Meulink et al. |
| 6,576,014 | B2 | 6/2003 | Shetty |
| 6,676,706 | B1 | 1/2004 | Mears et al. |
| 6,685,987 | B2 | 2/2004 | Shetty |
| 6,695,884 | B1 | 2/2004 | Townley |
| 6,994,731 | B2 | 2/2006 | Howie |
| 7,001,672 | B2 | 2/2006 | Justin et al. |
| 2002/0133234 | A1 | 9/2002 | Sotereanos |
| 2002/0177901 | A1 | 11/2002 | Howie |
| 2003/0074080 | A1 | 4/2003 | Murray |
| 2004/0054419 | A1 | 3/2004 | Serra et al. |
| 2005/0278030 | A1 | 12/2005 | Tornier et al. |
| 2006/0004465 | A1 | 1/2006 | Bergin et al. |
| 2006/0173549 | A1 | 8/2006 | Ragbir |
| 2006/0276906 | A1 | 12/2006 | Hoag et al. |
| 2007/0112433 | A1 | 5/2007 | Frederick et al. |

FOREIGN PATENT DOCUMENTS

| | | |
|---|---|---|
| DE | 8901018 U1 | 3/1989 |
| EP | 0363019 A2 | 4/1990 |
| EP | 0485311 A1 | 5/1992 |
| FR | 2575383 A1 | 7/1986 |
| FR | 2631543 A1 | 11/1989 |
| FR | 2645012 A1 | 10/1990 |
| FR | 2677879 A1 | 12/1992 |
| FR | 2726473 A1 | 5/1996 |
| FR | 2844994 A1 | 4/2004 |
| GB | 2216425 | 10/1989 |
| WO | WO94/16649 A1 | 8/1994 |
| WO | WO94/20046 A1 | 9/1994 |
| WO | WO97/41809 A1 | 11/1997 |

OTHER PUBLICATIONS

Surgical Technique—Zimmer Epoch® Hip Prosthesis 97-4075-02 Rev, Zimmer, Inc. 2002, 14 pages.

Brochure—Zimmer VerSys Hip System, Fiber Metal Taper HP Prosthes, Versatile Total Hip Solutions Using Proven Designs and Enhanced Fixation, 97-7862-01 20MIP, Zimmer, Inc. 1997, 4 pages.

Brochure—Zimmer VerSys Hip System, Cemented Hip Prosthesis, Traditional Design, Innovative Features, 97-7853-01 16MIL, Zimmer, Inc. 1999, 4 pages.

Brochure - Zimmer VerSys Hip System, LD/Fx Hip Prostheses, Versatile Solutions for Total and Partial Hip Replacement, 97-7831-01 Rev. 1, 15MM, Zimmer, Inc. 1998, 4 pages.

Page, John "Included Angle" 2007. The Math Open Reference Project. http://www.mathopenref.com/angleincluded.html.

Invitation to Pay Additional Fees and Partial Search Report mailed Mar. 2, 2009, in related International Patent Application No. PCT/US2007/064288.

Office Action mailed Jul. 7, 2009 in U.S. Appl. No. 11/353,392.

Restriction Requirement mailed Jul. 30, 2008 in U.S. Appl. No. 11/687,862.

Election filed Aug. 7, 2008 in U.S. Appl. No. 11/687,862.

Restriction Requirement mailed Mar. 12, 2009 in U.S. Appl. No. 11/687,862.

Election filed Apr. 6, 2009 in U.S. Appl. No. 11/687,862.

Office Action mailed Aug. 22, 2008 in U.S. Appl. No. 11/687,862.

Response filed Dec. 12, 2008 to the Office Action mailed Aug. 22, 2008 in U.S. Appl. No. 11/687,862.

Office Action mailed Apr. 17, 2009 in U.S. Appl. No. 11/687,862.

Response filed Jul. 24, 2009 to the Office Action mailed Aug. 22, 2008 in U.S. Appl. No. 11/687,862.

Surgical Technique—Zimmer VerSys Cemented, Cemented Plus, and Cemented CT Hip Prostheses, Zimmer, Inc., 18 pages, Copyright 1997.

\* cited by examiner

FIG_1

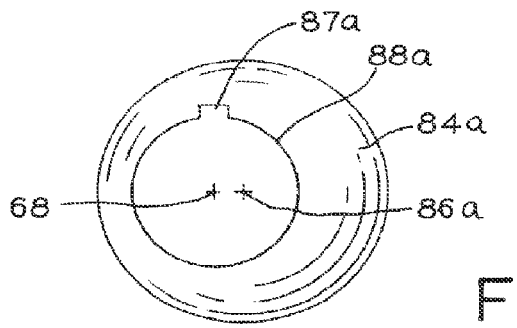
FIG_15
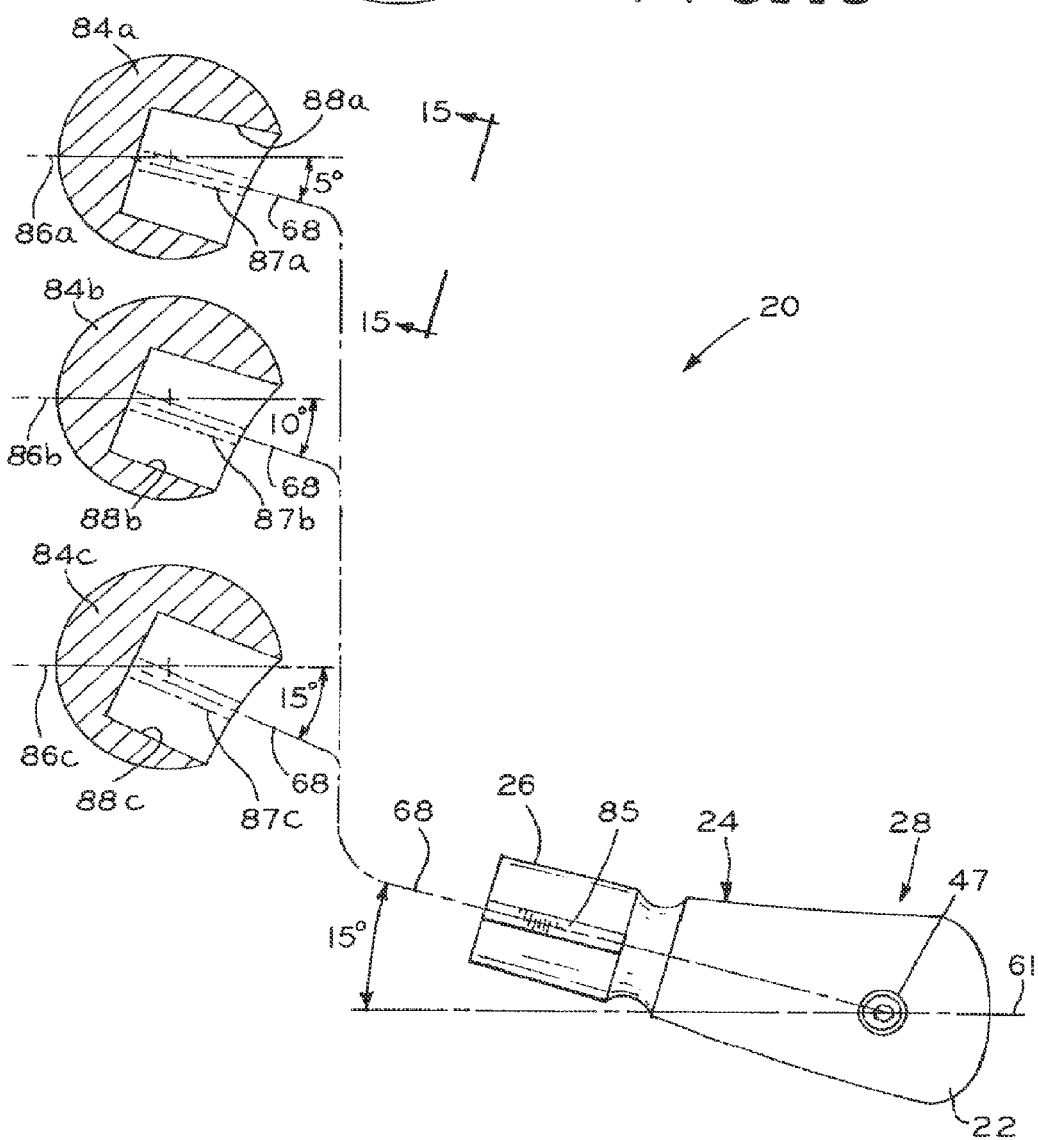
FIG_14

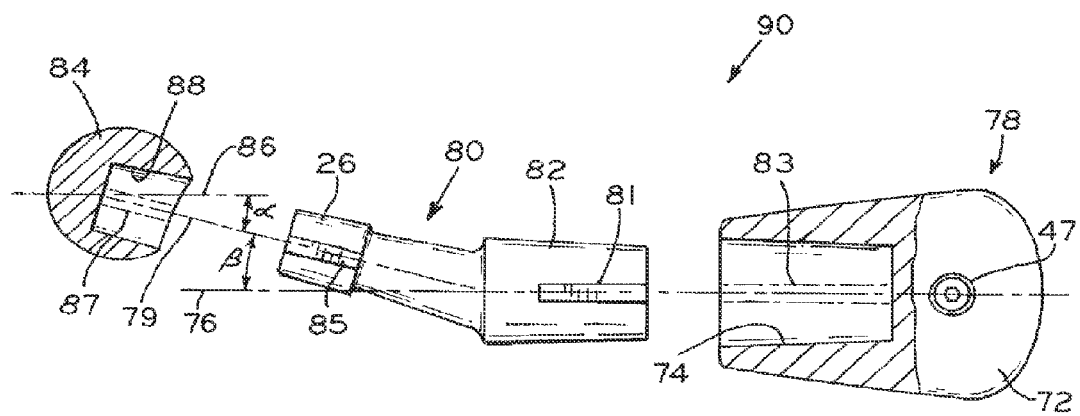
FIG_16
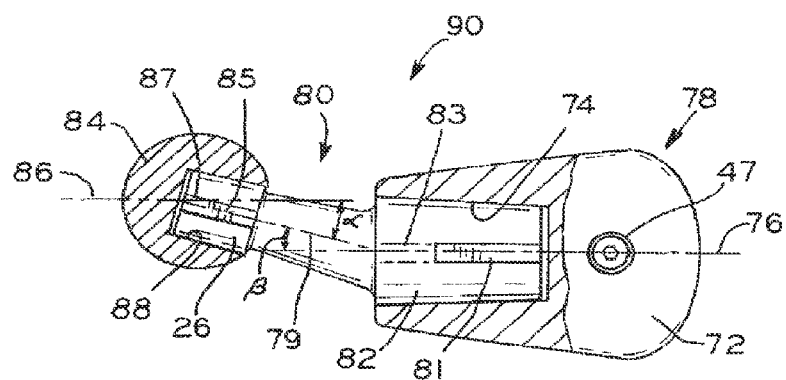
FIG_17

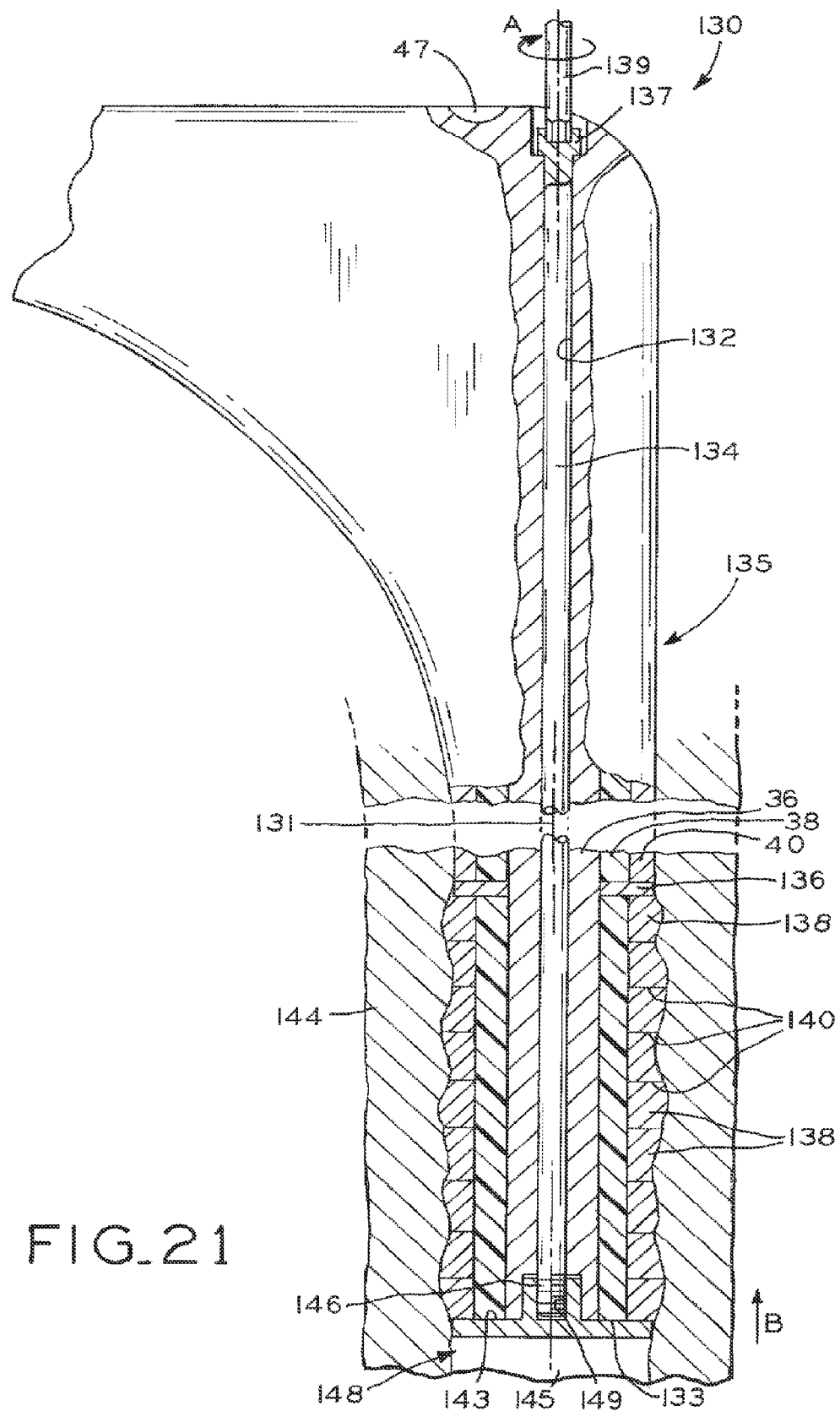
FIG_21

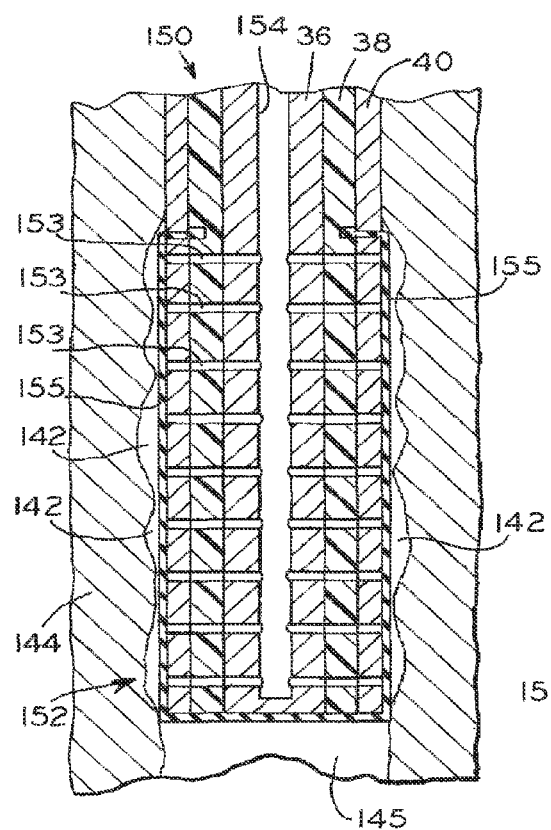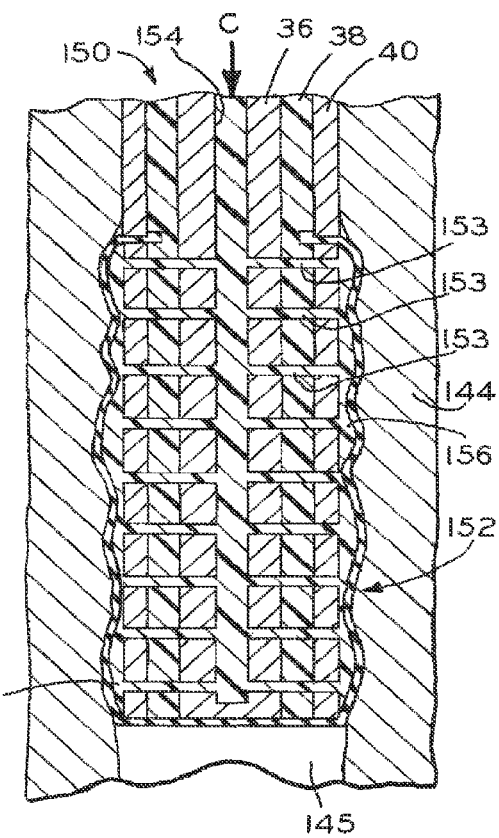
FIG_22    FIG_23

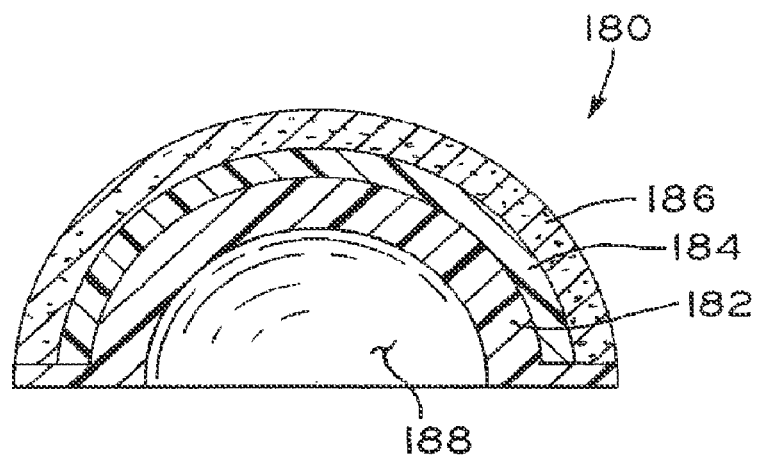
FIG_25
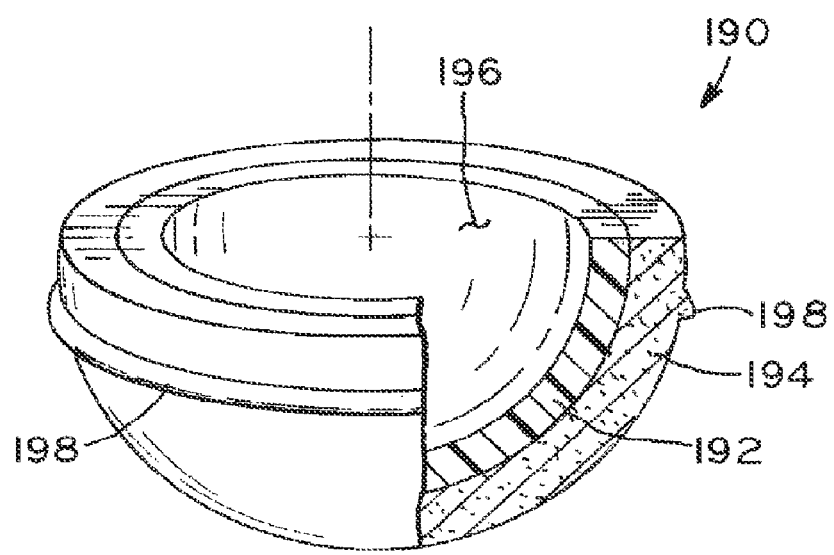
FIG_26

PROSTHETIC HIP IMPLANTS

CROSS REFERENCE TO RELATED APPLICATIONS

This application is a continuation of co-pending U.S. patent application Ser. No. 11/687,862, filed Mar. 19, 2007, entitled PROSTHETIC HIP IMPLANTS, which claims the benefit of U.S. Provisional Patent Application Ser. No. 60/783,880, filed Mar. 20, 2006, the disclosures of which are hereby expressly incorporated herein by reference.

BACKGROUND

1. Field of the Invention

The present invention relates to prosthetic hip implant components, including a hip stem for implantation in the proximal femur and an acetabular cup for implantation in the acetabulum. In particular, the present invention relates to prosthetic hip stems and acetabular cups which include improved features adapted to achieve more optimized results with certain types of patient anatomy, such as the anatomy of female patients.

2. Description of the Related Art

Orthopedic implants are commonly used to replace some or all of a patient's hip joint in order to restore the use of the hip joint, or to increase the use of the hip joint, following deterioration due to aging or illness, or injury due to trauma. In a hip replacement, or hip arthroplasty procedure, a femoral component is used to replace a portion of the patient's femur, including the femoral neck and head. The femoral component is typically a hip stem, which includes a stem portion positioned within the prepared femoral canal of the patient's femur and secured via bone cement, or by a press-fit followed by bony ingrowth of the surrounding tissue into a porous coating of the stem portion. The hip stem also includes a neck portion adapted to receive a prosthetic femoral head. The femoral head is received within a prosthetic acetabular component, such as an acetabular cup received within the prepared recess of the patient's acetabulum.

One known hip stem includes a core formed of either a cobalt-chromium-molybdenum alloy or titanium, and a porous surface layer in the form of a matrix of small metallic beads or a wire mesh. Typically, the porous surface layer is sintered to the core by heating the core and the porous surface layer to a high temperature in order to cause the porous surface layer and core to fuse, melt, or bond together along their interface. U.S. Pat. Nos. 6,395,327, 6,514,288, and 6,685,987, each assigned to the assignee of the present invention and hereby incorporated by reference, disclose various methods of enhancing the fatigue strength and the connection between the core and the porous surface layer of the foregoing types of hip stems.

SUMMARY

The present invention provides prosthetic hip stems and acetabular cups for use in prosthetic hip joints. The hip stem may include a core having a stem portion and a neck portion, a polymer matrix layer substantially covering the stem portion of the core, and a porous metal layer substantially covering the polymer matrix layer. The polymer matrix layer connects the core and the porous metal layer and provides a stiffness for the hip stem which more closely mimics the stiffness of bone than do known hip stems. The hip stems and acetabular cups additionally include a number of improvements adapted for more optimized results with certain types of patient anatomy, such as the anatomy of female patients, for example.

In one form thereof, the present invention provides a prosthetic hip stem, including a stem portion having a proximal end and a distal end, the stem portion defining a medial/lateral plane; and a neck portion projecting from the proximal end, the neck portion having a longitudinal axis therealong which is oriented at a first angle between 13 degrees and 25 degrees anteriorly with respect to the medial/lateral plane.

In another form thereof, the present invention provides a prosthetic hip stem, including a stem portion having a proximal end and a distal end, the stem portion defining a medial/lateral plane therethrough; a neck portion projecting from the proximal end of the stem portion and having a first, longitudinal axis; and a head portion of substantially spherical shape and connected to the neck portion along the first axis, the head portion having a center disposed on second axis which is disposed at a second angle of between 1 and 25 degrees anteriorly with respect to the first axis.

In a further form thereof, the present invention provides a prosthetic hip stem, including a stem portion having a proximal end and a distal end, and a first, proximal/distal longitudinal axis; and a neck portion projecting from the proximal end, the neck portion having a second longitudinal axis therealong which is oriented at a first angle of between 90 and 145 degrees with respect to the first axis.

In another form thereof, the present invention provides a prosthetic hip stem, including a stem portion having a proximal end and a distal end; and a distal end fixation mechanism operable between a first condition wherein the distal end of the stem portion has a first width with respect to at least one of a medial/lateral plane and an anterior/posterior plane of the stem portion and a second condition wherein the distal end of the stem portion has a second width with respect to at least one of the medial/lateral plane and the anterior/posterior plane, the second width greater than the first width.

In another form thereof, the present invention provides an acetabular cup, including a substantially hemispherical cup portion made of a relatively thin, flexible porous metal; and a liner fitted within the cup portion, the liner including a substantially hemispherical bearing surface.

In another form thereof, the present invention provides an acetabular cup, including a liner including a substantially hemispherical bearing surface; a porous metal cup portion; and an intermediate layer disposed between the liner and the porous metal cup portion, the intermediate layer formed of a polymer matrix.

In another form thereof, the present invention provides an acetabular cup, including a liner including a substantially hemispherical bearing surface; and a cup portion including an outer hemispherical portion including a substantially annular loading rib.

In another form thereof, the present invention provides a prosthetic hip stem, including a proximal end including a core, a polymer matrix layer covering at least a portion of the core, and a porous metal layer substantially covering the polymer matrix layer; and a distal end including a core and a porous metal layer substantially covering the core.

In a further form thereof, the present invention provides a prosthetic hip stem, including a proximal end and a distal end; an inner core; a porous metal outer layer; and an elongated cavity formed in the distal end, wherein the distal end is flexible.

BRIEF DESCRIPTION OF THE DRAWINGS

The above-mentioned and other features of this disclosure, and the manner of attaining them, will become more apparent and will be better understood by reference to the following description of embodiments taken in conjunction with the accompanying drawings, wherein:

FIG. 14 is a proximal end view of components of a modular hip stem system, including an integral stem portion and neck portion, and a plurality of anteverted modular femoral heads which may be used with the hip stem;

FIG. 15 is an end view of a modular femoral head taken along line 15-15 of FIG. 14;

FIG. 16 is an exploded, partially sectioned proximal end view of components of a modular hip stem system showing a hip stem portion, an anteverted modular neck portion, and an anteverted modular femoral head;

FIG. 17 is an assembled, partially sectioned proximal end view of the components of the modular hip stem system of FIG. 16;

FIG. 21 is a cross-sectional view of a portion of the hip stem of FIG. 20, further illustrating the distal end fixation mechanism in an expanded condition;

FIG. 22 is a cross-sectional view of a portion of a hip stem within the diaphysis of a femur, further illustrating an alternative embodiment of a distal end fixation mechanism in a non-expanded condition;

FIG. 23 is a cross-sectional view of a portion of the hip stem of FIG. 22, further illustrating the distal end fixation mechanism in an expanded condition;

FIG. 25 is a sectional view of an acetabular cup according to another embodiment;

FIG. 26 is a partial sectional view of an acetabular cup according to a further embodiment;

Corresponding reference characters indicate corresponding parts throughout the several views. The exemplifications set out herein illustrate embodiments of the disclosure, and such exemplifications are not to be construed as limiting the scope of the invention in any manner.

DETAILED DESCRIPTION

Figure 1:
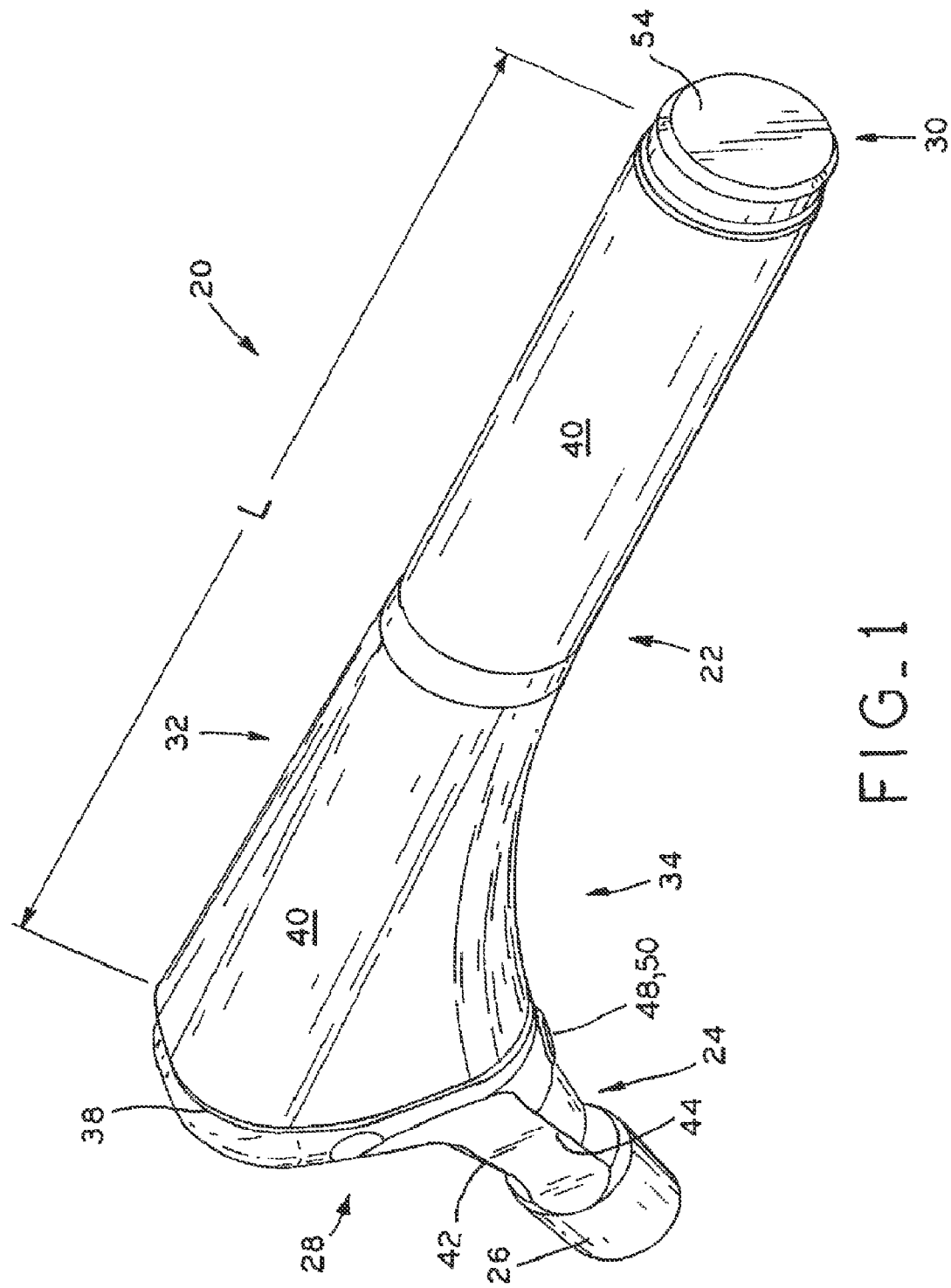
FIG. 1 is a first isometric view of a hip stem according to the present invention.

Referring to FIGS. 1-5, a prosthetic hip stem 20 according to the present invention is shown, which generally includes stem portion 22, and neck portion 24 extending at a generally obtuse angle from stem portion 22 and including a tapered femoral head fitting 26. Stem portion 22 of hip stem 20 is received within a prepared femoral canal of a patient's femur to anchor hip stem 20 within the patient's femur. As discussed below, a femoral head component is fitted on femoral head fitting 26, and is in turn received within a prosthetic acetabular component, such as an acetabular cup seated within a prepared recess in the patient's acetabulum, to thereby provide an articulating, prosthetic hip joint. Hip stem 20 further defines proximal end 28, distal end 30, lateral side 32, medial side 34, as well as opposing anterior and posterior sides depending upon whether hip stem 20 is used with a patient's right or left femur.

Figure 3:
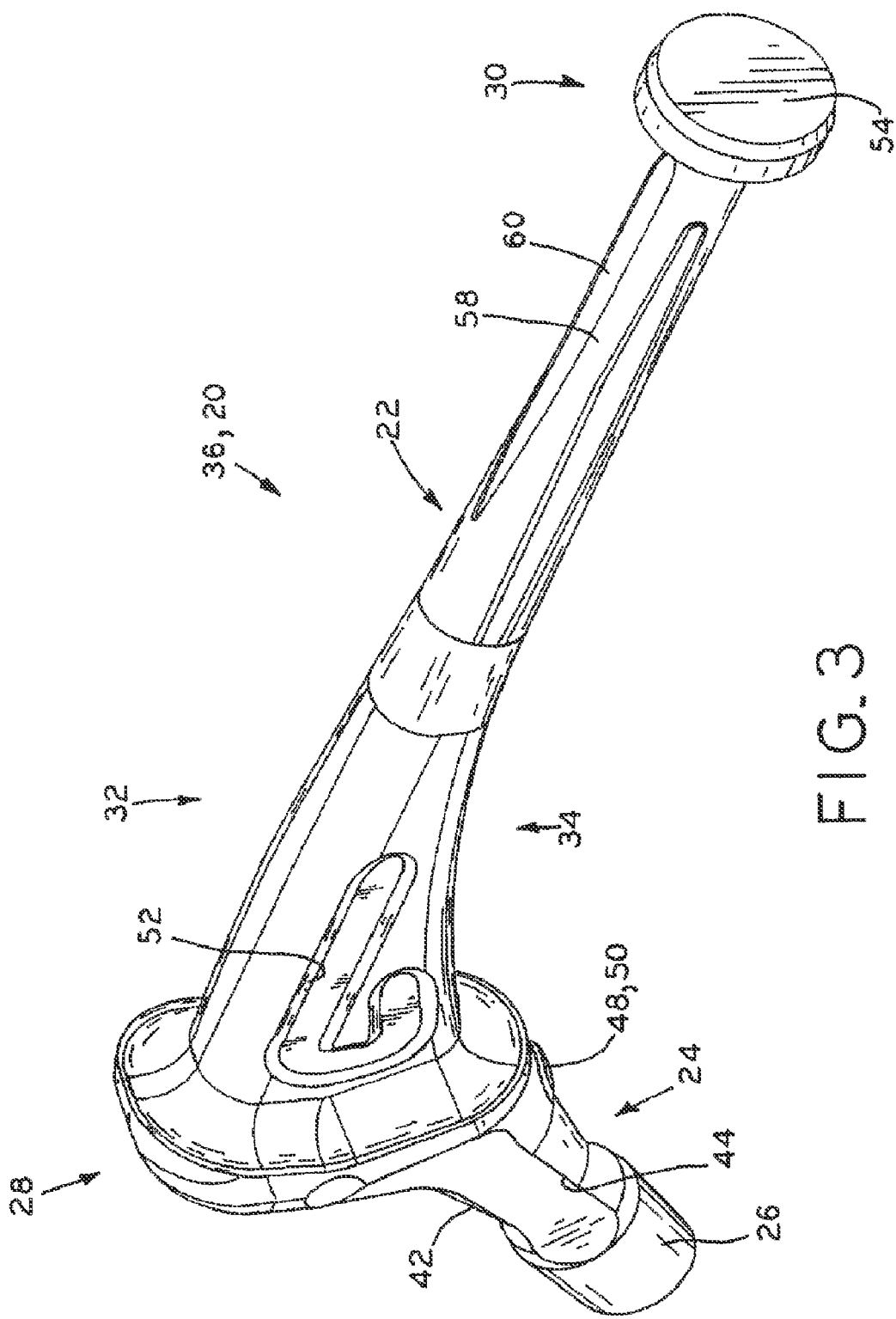
FIG. 3 is a first isometric view of the core of the hip stem of FIGS. 1 and 2.
Figure 4:
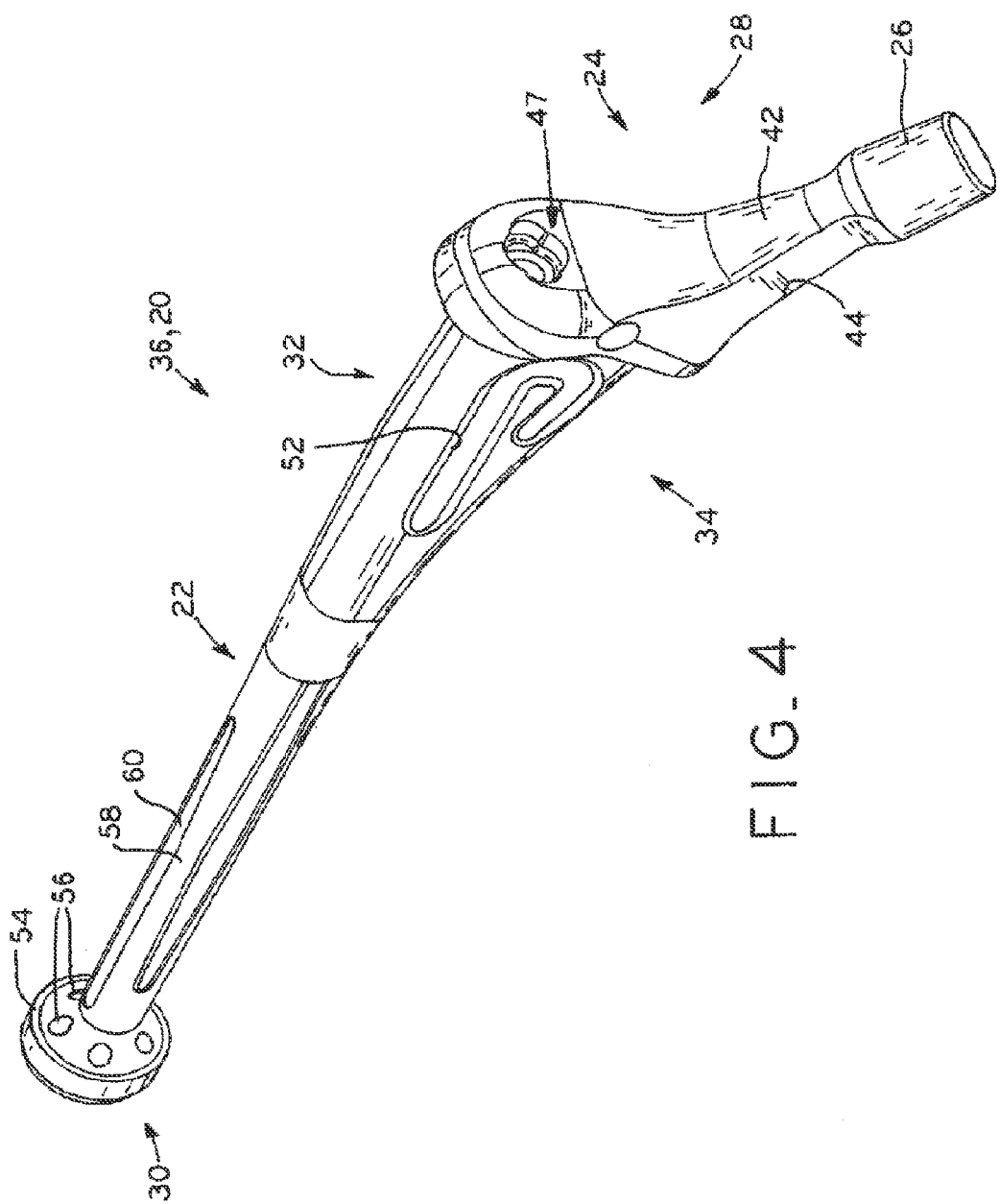
FIG. 4 is a second isometric view of the core of the hip stem of FIGS. 1 and 2.
Figure 5:
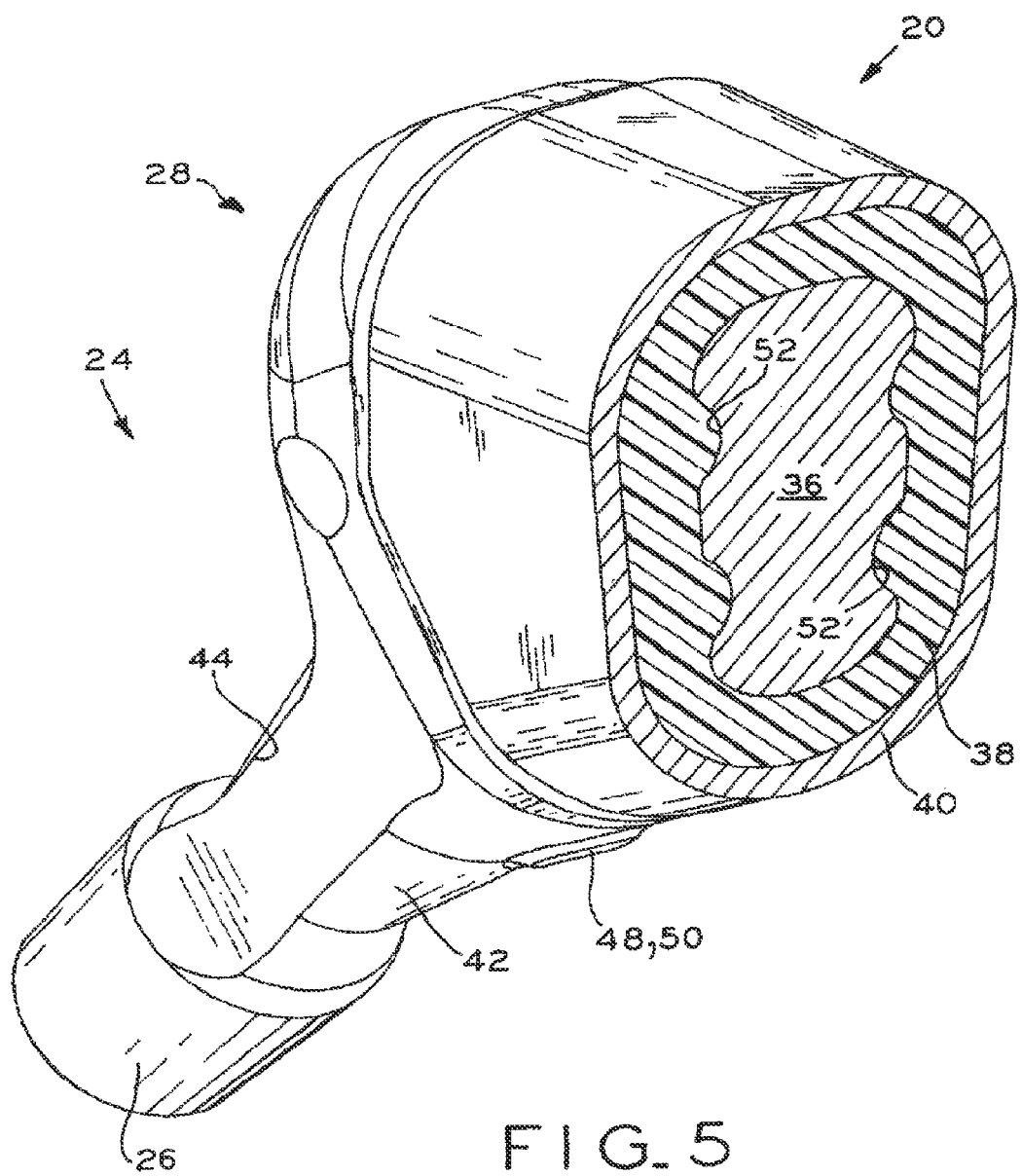
FIG. 5 is a sectional view through the hip stem, taken along line 5-5 of FIG. 2.

Referring particularly to FIGS. 3-5, hip stem 20 generally includes a substrate or core 36 generally defining stem portion 22 and neck portion 24 and, as best seen in FIG. 5, a polymer matrix layer 38 substantially covering stem portion 22 of core 36, and a porous metal layer 40 substantially covering polymer matrix layer 38. Polymer matrix layer 38 and porous metal layer 40 may cover substantially all of stem portion 22 of core 36, or alternatively, may cover only selected portions thereof, as desired. In one embodiment, stem portion 22 has a length L (FIG. 1) extending generally from proximal end 28 to distal end 30, and, in one embodiment, stops slightly short of each end 28, 30 by approximately 0.3 inches. Porous metal layer 40 extends along length L from approximately 10, 20, 30% thereof or as much as 70, 80, 90, or 95% thereof. In one embodiment, porous metal layer 40 extends along stem portion 22 for approximately 33% of the length thereof. In another embodiment, porous metal layer 40 covers approximately 33% of proximal end 28 of stem portion 22, i.e., a midcoat porous stem.

Core 36 may be made from a cobalt-chromium-molybdenum alloy or a titanium alloy, for example, via a forging or casting process, followed by machining to achieve a desired shape or profile. Polymer matrix layer 38 may be formed of an inert polyaryletherketone ("PAEK") polymer such as, for example, polyetheretherketone ("PEEK"). Porous metal layer 40 may be a metal wire mesh of titanium fibers, or alternatively, may also comprise a metal bead matrix or other porous metal structures produced in accordance with Trabecular Metal™ technology of Zimmer, Inc. of Warsaw, Ind., for example.

Hip stem 20 may be manufactured as follows. First, core 36 is forged, followed by machining core 36 after forging to form a desired shape or profile for core 36. Core 36 is then grit blasted to sufficiently roughen its surface, and then is heat treated to facilitate polymer flow across core 36 during the injection molding process. Thereafter, core 36 is positioned within an injection molding machine with stem portion 22 of core 36 positioned within porous metal layer 40, with a gap provided therebetween. Thereafter, polymer matrix layer 38 is injected into the space between core 36 and porous metal layer 40 through suitable gates, with polymer matrix layer 38 permeating into porous metal layer 40 and into the surface of stem portion 22 of core 36 via grooves 52, dimples 56, ridges 58, and/or flats 60. Upon cooling of polymer matrix layer 38, porous metal layer 40 is firmly bonded or secured to stem portion 22 of core 36. Advantageously, core 36 is not subjected to a sintering process to apply porous metal layer 40, thereby maintaining the fatigue strength of core 36.

Figure 2:
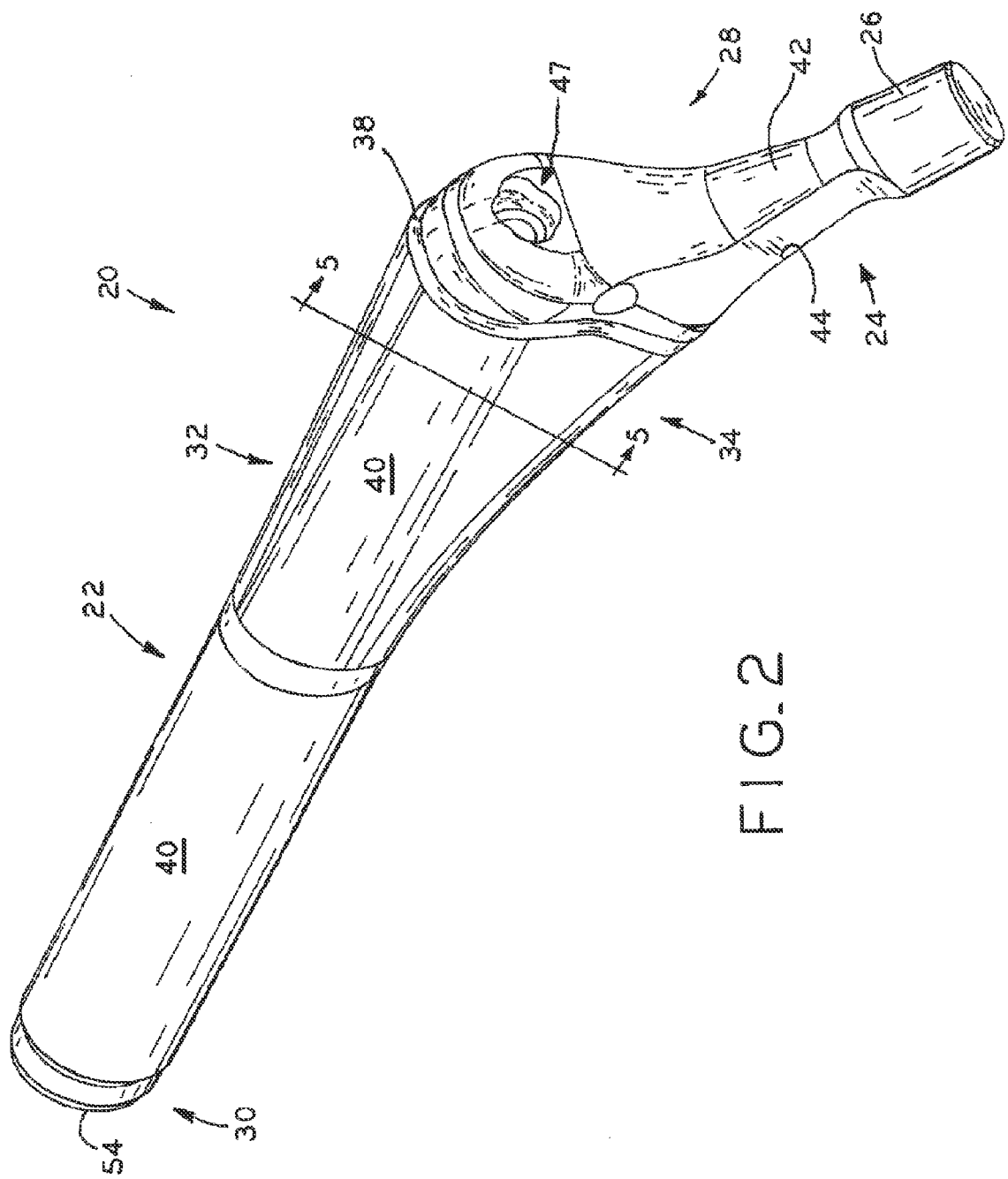
FIG. 2 is a second isometric view of the hip stem of FIG. 1.
Figure 6:
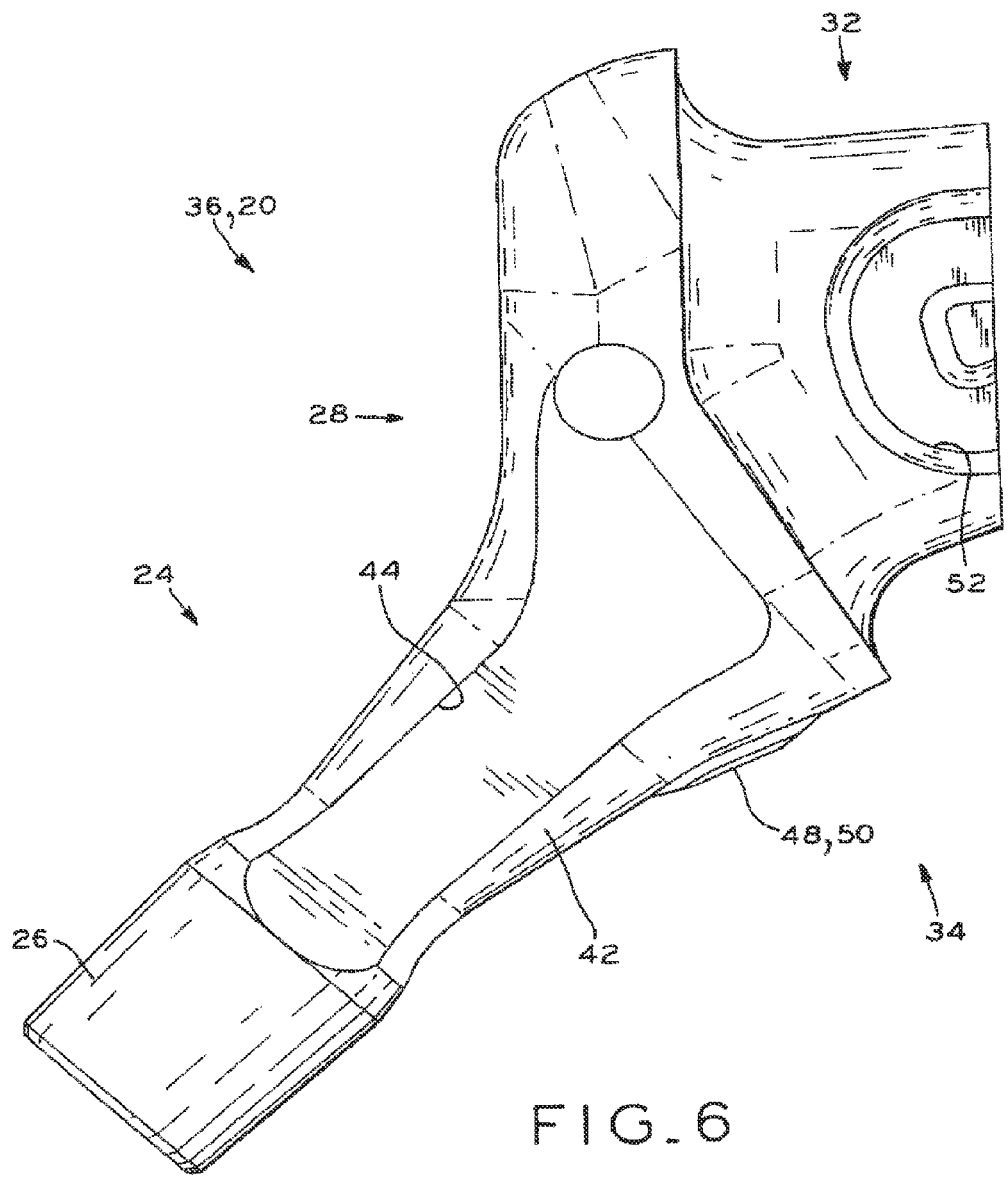
FIG. 6 is a side view of the proximal end of the hip stem, showing the contoured neck portion and the version indicator feature.
Figure 7:
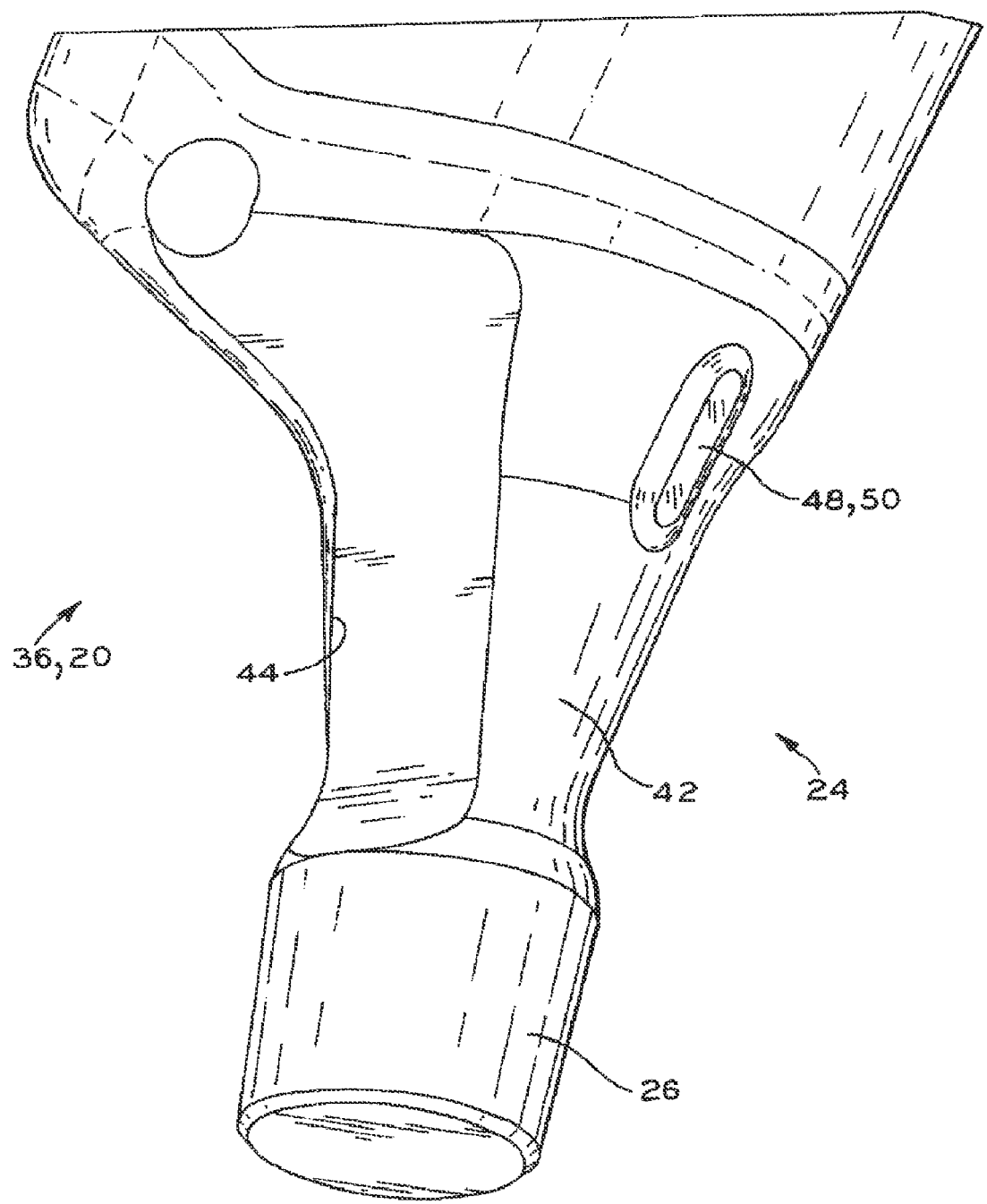
FIG. 7 is an isometric view of the proximal end of the hip stem, showing the contoured neck portion.
Figure 8:
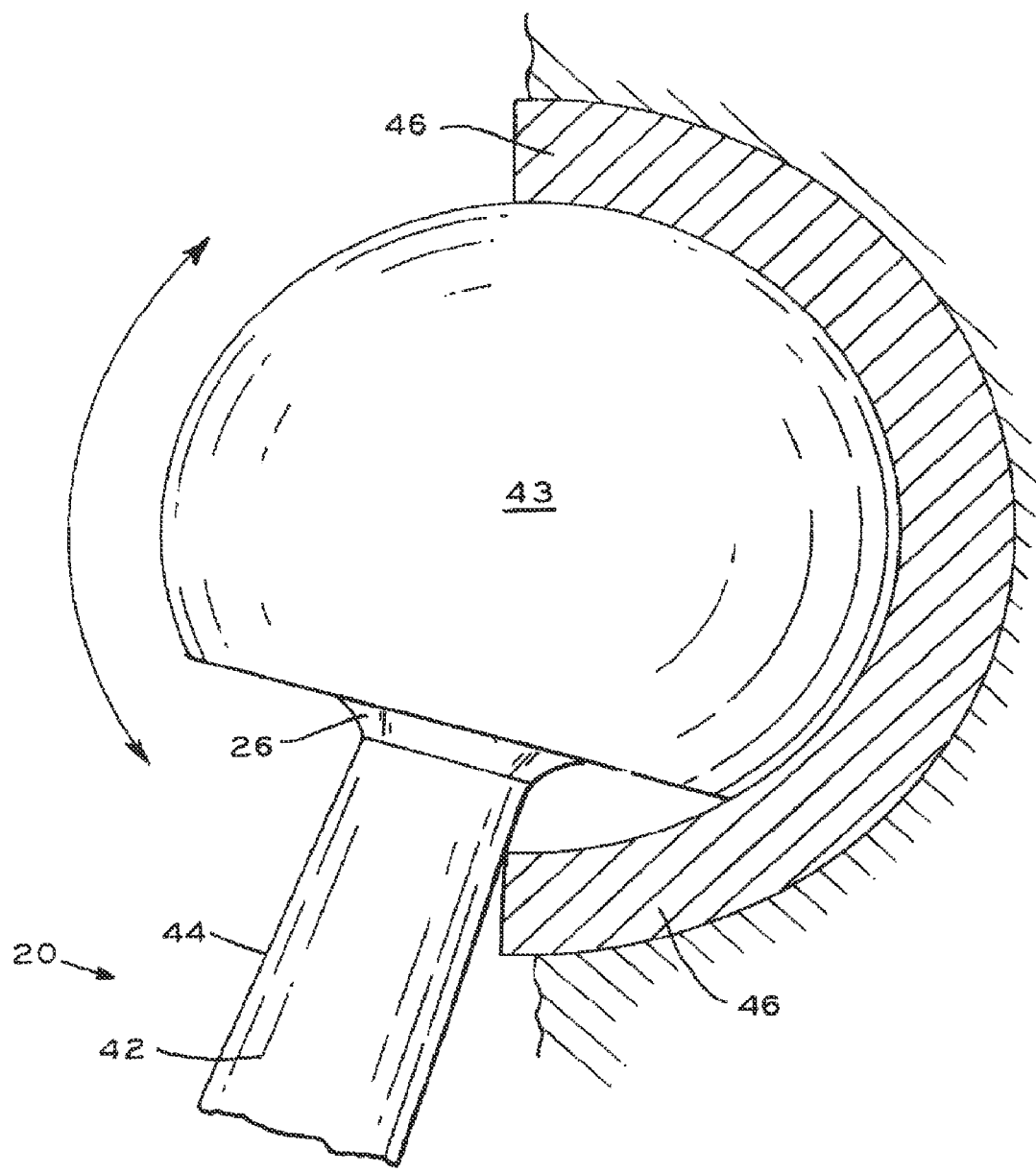
FIG. 8 is a side view of the proximal end of the hip stem, shown with a femoral head thereof fitted within an acetabular cup which is in turn positioned within an acetabulum, and illustrating the relatively large degree of articulating movement possible therebetween.

Referring to FIGS. 6-8, neck portion 24 of hip stem 20 is contoured to allow for increased articulating movement of hip stem 20 with respect to an acetabular component in a prosthetic hip joint, as illustrated in FIG. 8. As shown in FIGS. 6 and 7, neck portion 24 of hip stem 20 includes a neck section 42 which extends between stem portion 22 and femoral head fitting 26. Neck section 42 is shaped with a relatively thin or slender profile, having a diameter along a substantial portion thereof which is less than the maximum diameter of femoral head fitting 26. In particular, neck section 42 may include a plurality of scalloped recesses 44 therearound which may be formed by removal of material from the original forging of core 36 by machining. As shown in FIG. 8, the thin or slender profile of neck section 42 allows for an increased degree of angular, articulating movement of hip stem 20 with respect to the acetabular component in a prosthetic hip joint when a prosthetic femoral head 43 is fitted on fitting 26 of stem 20 and received within the acetabular component, which is shown in FIG. 8 as an acetabular cup 46 positioned within a prepared recess in the surrounding acetabulum. Also, as shown in FIGS. 2 and 4, neck portion 24 of core 36 of hip stem 20 may include an instrument engagement fitting 47 in proximal end 28 thereof within which an instrument (not shown) may be engaged to aid in driving hip stem 20 into the prepared femoral canal of a patient's femur.

Referring to FIGS. 6 and 7, neck portion 24 of hip stem 20 also includes a version indicator feature 48, which is shown herein as a bump or protrusion 50 projecting from medial side 34 of neck portion 24 of hip stem 20. As explained below, version indicator feature 48 is a tactile feature on hip stem 20 which may be felt by a surgeon during implantation of hip stem 20 to aid the surgeon in positioning hip stem 20 according to a desired version or alignment. U.S. Pat. No. 6,676,706, assigned to the assignee of the present invention and incorporated herein by reference, discloses a method for performing a "non-open", or minimally invasive, total hip arthroplasty. In the foregoing method, a small anterior incision is made for preparing a recess or seat in the acetabulum for receiving an acetabular cup, which is inserted and positioned within the acetabulum through the anterior incision. A small posterior incision is also made for preparing the femur and for receiving a hip stem, such as hip stem 20, which is positioned within the prepared femoral canal of the femur. During this and other minimally invasive procedures, the insertion of the hip stem into the prepared femoral canal may not be directly viewable by the surgeon, or may be only partially viewable by the surgeon, such as through the anterior incision.

Figure 9:
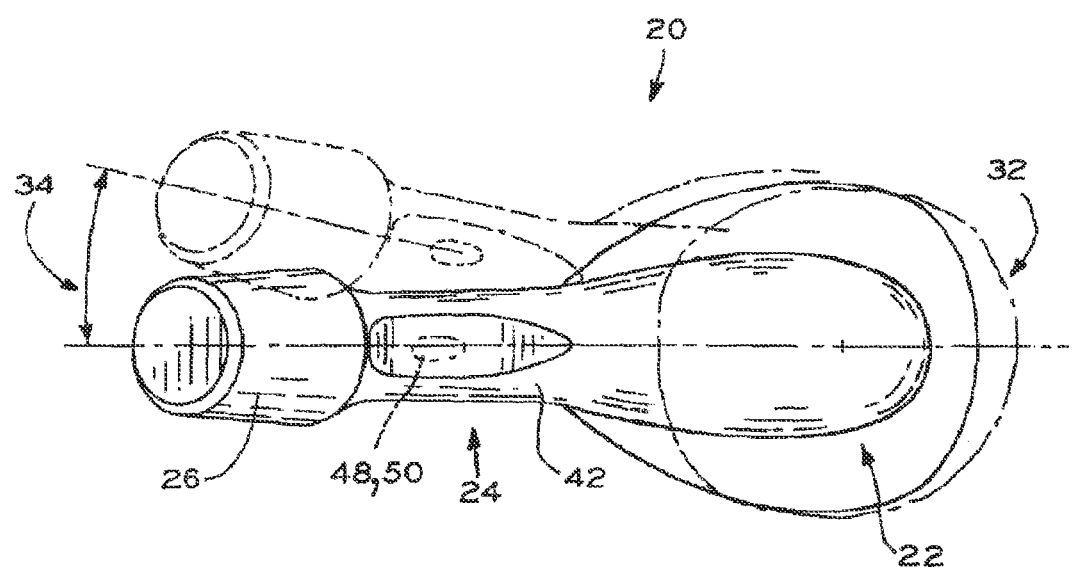
FIG. 9 is a schematic top view of the hip stem, showing relative neutral and anteversion positions of the hip stem with respect to a patient in solid and dashed lines, respectively.

Referring to FIG. 9, upon insertion of hip stem 20 into the prepared femoral canal through a posterior incision, a surgeon may feel protrusion 50 of version indicator element 48 by inserting the surgeon's fingers through the anterior incision, for example, to position hip stem 20 in an anteversion alignment, shown in dashed lines in FIG. 9, in which neck portion 24 of hip stem 20 is rotated approximately 12° to 14° anteriorly with respect to stem portion 22 from the neutral version, or direct medial/lateral, alignment shown in solid lines in FIG. 9. Optionally, according to some surgical procedures, the surgeon may tactilely align protrusion 50 of version indicator element 48 with respect to one or more grooves which are cut in the medial calcar of the prepared femur in order to position hip stem 20. Protrusion 50 of version indicator element 48 may also be used by the surgeon to position hip stem 20 in a position other than in an anteversion alignment if needed. Thus, protrusion 50 of version indicator element 48 advantageously allows the surgeon to position hip stem 20 according to a desired alignment during a minimally invasive hip arthroplasty procedure without direct visualization of hip stem 20.

Although version indicator feature 48 is shown herein as bump or protrusion 50, other tactile elements may be used, such as a recess, a group of recesses, or a ridge or a group of ridges, for example, in medial side 34 of neck portion 24 of hip stem 20, or at another location or locations on neck portion 24 of hip stem 20.

Figure 10:
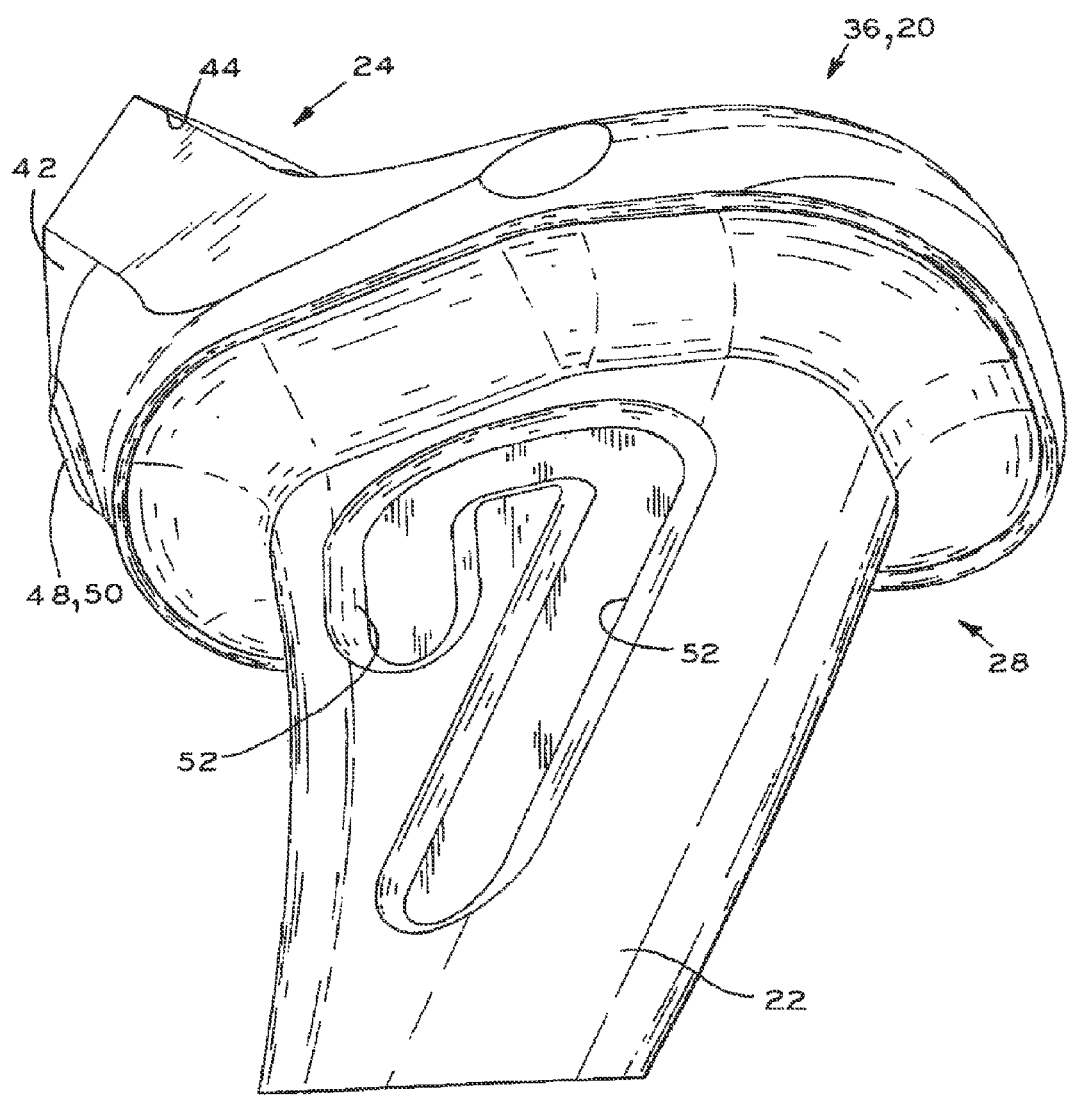
FIG. 10 is an isometric view of the proximal end of the core of the hip stem, showing the curved groove therein.
Figure 11:
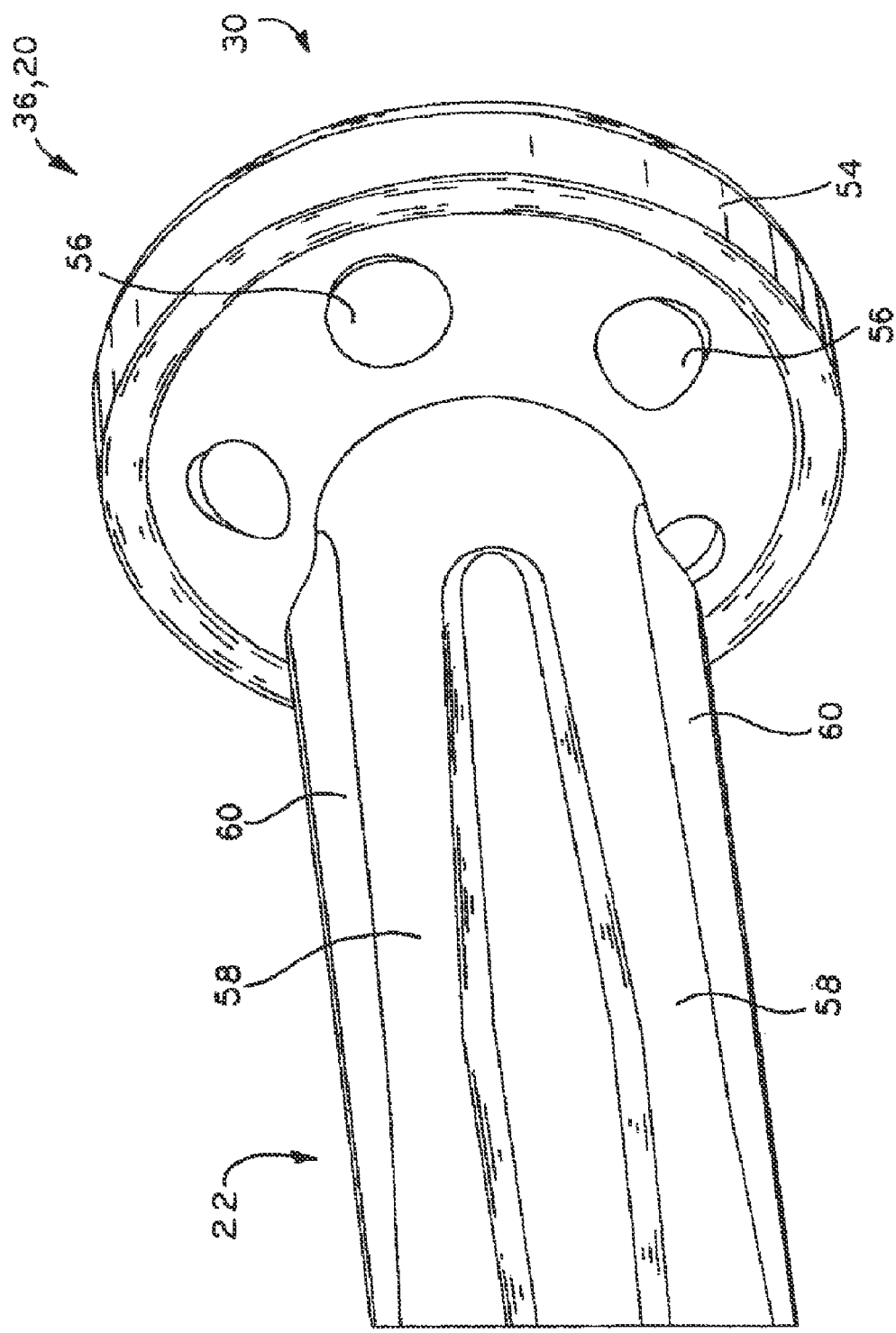
FIG. 11 is an isometric view of a portion of the distal end of the core of the hip stem, showing the distal boss of the core, including a plurality of dimples around the boss and a plurality of ridges in the stem portion of the core.

Referring to FIGS. 10 and 11, core 36 includes a plurality of features for enhancing the mechanical interconnection between core 36 and polymer matrix layer 38. As shown in FIG. 10, proximal end 28 of stem portion 22 of core 36 includes a curved, generally "candy cane"-shaped or "number 7"-shaped groove 52 on one or both of the anterior and posterior sides thereof. During manufacture of hip stem 20, in which the material of polymer matrix layer 38 is injected into the space between core 36 and porous metal layer 40, the material of polymer matrix layer 38 flows into and substantially fills grooves 52 to form a robust mechanical interconnection between core 36 and polymer matrix layer 38 upon curing of the material. The mechanical interconnection resists relative movement between core 36 and polymer matrix layer 38, such as rotational movement, responsive to torsional and/or other types of loading which may be imposed upon core 36 when hip stem 20 is used in a hip joint, and in particular, after porous metal layer 40 becomes substantially fused to the surrounding femoral bone tissue.

Referring to FIG. 11, distal end 30 of core 36 includes a boss 54 which provides a rigid leading surface for insertion of hip stem 20 into a prepared femoral canal. Boss 54 also includes a plurality of dimples 56 formed circumferentially therearound. During manufacture of hip stem 20, in which the material of polymer matrix layer 38 is injected into the space between core 36 and porous metal layer 40, the material of polymer matrix layer 38 flows into and substantially fills dimples 56 to form a robust mechanical interconnection between core 36 and polymer matrix layer 38 upon curing of the material. The mechanical interconnection also resists relative movement, such as relative rotational movement, between core 36 and polymer matrix layer 38 responsive to torsional and/or other types of loading upon core 36 after hip stem 20 is implanted.

Still referring to FIG. 11, stem portion 22 of core 36 may additionally include further features to enhance the mechanical interconnection between core 36 and polymer matrix layer 38, such as ridges 58 and/or flats 60, or other projecting or recessed features in core 36 such as grooves, cavities, bores, dimples, bumps, protuberances, protrusions, or other features which may be formed in core 36 by forging or post-forging machining, for example. Ridges 58 and flats 60 extend longitudinally along core 36 and resist relative movement, such as relative rotational movement, between core 36 and polymer matrix layer 38 responsive to torsional and/or other types of loading which may be imposed upon core 36 as described above.

As discussed in further detail below, the present inventors have developed a number of improvements to hip stems and acetabular cups in order to provide more optimized results with certain types of patient anatomy, such as female anatomy.

The hip stems and acetabular cups described herein may be implanted according to surgical techniques described in U.S. Pat. No. 6,676,706, issued Jan. 13, 2004; U.S. Pat. No. 6,860,903, issued Mar. 1, 2005; U.S. Pat. No. 6,953,480, issued Oct. 11, 2005; U.S. Pat. No. 6,991,656, issued Jan. 31, 2006; abandoned U.S. patent application Ser. No. 10/929,736, filed Aug. 30, 2004; currently pending U.S. patent application Ser. No. 10/952,301, filed Sep. 28, 2004; currently pending U.S. patent application Ser. No. 11/235,286, filed Sep. 26, 2005; and currently pending U.S. patent application Ser. No. 11/105,080, filed Apr. 13, 2005, all titled METHOD AND APPARATUS FOR PERFORMING A MINIMALLY INVASIVE TOTAL HIP ARTHROPLASTY and all assigned to the assignee of the present application, the disclosures of which are hereby expressly incorporated herein by reference.

Known hip stems typically have an anteversion angle between the neck portion of the hip stem and the anatomical medial/lateral plane of from 1 to 12 degrees, for example. The present inventors have observed that for many patients, particularly certain female patients, a greater anteversion angle between the neck portion of the hip stem and the anatomical medial/lateral plane, and/or an anteversion angle between the femoral head portion and the neck portion of the hip stem, would provide more optimum anatomical benefits.

Figure 12:
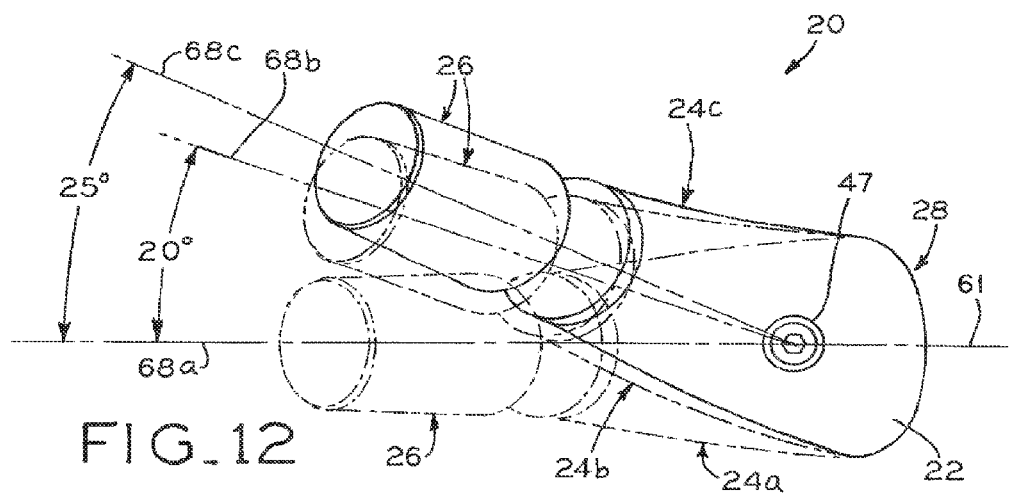
FIG. 12 is a schematic proximal end view of several hip stems each having an integral stem portion and neck portion and showing a range of possible anteversion angles for the neck portions.

Referring to FIG. 12, a top view of proximal end 28 of hip stem 20 is shown including stem portion 22 and neck portion 24 integrally formed with one another. Typical known hip stems include neck portion 24a with femoral head fitting 26, shown in dashed lines in FIG. 12, whose central longitudinal axis 68c coincides and is aligned with medial/lateral plane 61, i.e., neck portion 24a is angled approximately 0° anteriorly with respect to the anatomical medial/lateral plane 61 and therefore has a neutral version and lacks anteversion. Hip stem 20 also includes instrument engagement fitting 47 in proximal end 28 thereof within which an instrument (not shown) may be engaged to aid in driving hip stem 20 into the prepared femoral canal of a patient's femur. Although illustrated throughout as the intersection point between medial/lateral plane 61 and central longitudinal axis of the neck portion, fitting 47 may be located at any location on hip stem 20 to aid in driving hip stem 20 into the prepared femoral canal. As illustrated, however, fitting 47 provides a convenient location for the intersection of plane 61 with the central longitudinal axis of each neck portion.

In order to facilitate greater anteversion, hip stem 20 may include a neck portion 24 which is angled with respect to the anatomical medial/lateral plane 61. For example, hip stem 20 is shown in an anteversion alignment in solid lines in FIG. 12, in which neck portion 24c having femoral head fitting 26 is angled approximately 25° anteriorly with respect to stem portion 22 from the neutral version, or direct medial/lateral alignment. Central longitudinal axis 68c of neck portion 24c defines a 25° angle with medial/lateral plane 61. In another embodiment, hip stem 20 may include neck portion 24b with femoral head fitting 26, shown in dashed lines in FIG. 12, which is angled approximately 20° anteriorly with respect to stem portion 22 from the neutral version alignment, i.e., central longitudinal axis 68b of neck portion 24b defines a 20° angle with plane 61. Advantageously, the surgeon may choose a hip stem 20 from a plurality of hip stems 20 in a system to have a desired anteversion alignment corresponding to the patient-specific anatomy. The angle of anteversion may be selected to have neck portion 24 angled with respect to medial/lateral plane 61 between 0° and 25° or more and, more particularly, the hip stem may be selected from a plurality of hip stems in a system including hip stems having respective anteversion angles of as little as 13°, 14°, or 16° or as great as 21°, 23°, or 25° or more, for example, or any angle therebetween. In particular, many female patients may require a larger degree of anteversion alignment of neck portion 24 with respect to the anatomical medial/lateral plane 61 than is provided by known hip stem systems. As discussed above, a larger anteversion angle between the neck portion and the medial/lateral plane may provide more optimum anatomical benefits in certain patients, including certain female patients.

Figure 13:
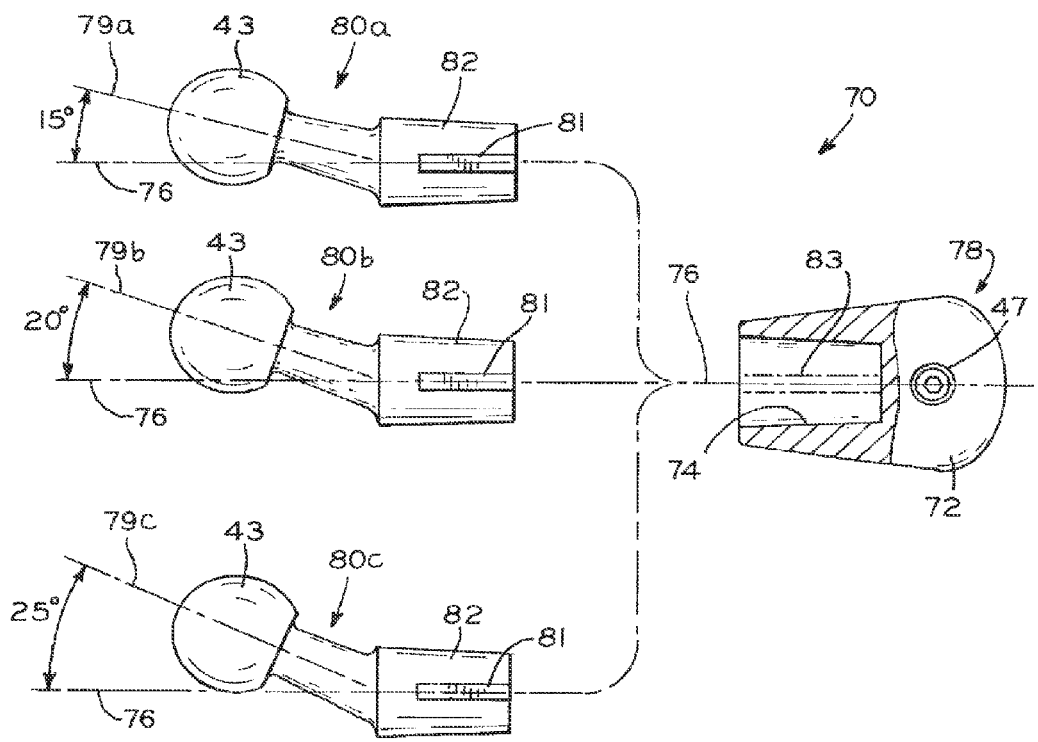
FIG. 13 is a proximal end view of components of a modular hip stem system, including a hip stem portion and a plurality of anteverted modular neck portions which may be used with the hip stem portion.

Referring to FIG. 13, a top view of components of a modular hip stem system are shown. Proximal end 78 of stem portion 72 of an alternative hip stem 70 is shown wherein, except as described below, hip stem 70 and stem portion 72 are substantially similar to hip stem 20 and stem portion 22 of FIGS. 1-5 described above. Proximal end 78 of stem portion 72 includes tapered recess 74 for mating engagement with a selected one of a plurality of modular neck portions 80. Each modular neck portion 80 includes tapered fitting portion 82 for mating with recess 74 upon assembly. Each modular neck portion 80 may also include an optional anti-rotation feature, shown as key 81, for engagement with another anti-rotation feature of hip stem 70, shown as groove 83 in recess 74 of stem portion 72, to prevent rotational movement between neck portion 80 and stem portion 72. Alternatively, each modular neck portion 80 and stem portion 72 may be provided with an oval engagement profile therebetween to provide anti-rotation. A substantially spherical femoral head 43 may be integrally formed with each modular neck portion 80 as shown in FIG. 13 or alternatively, each modular neck portion 80 may be coupled with a modular femoral head separately formed and attached to modular neck portion 80 via a tapered bore/fitting connection, for example, as described below.

Each neck portion 80 is oriented in an alignment which is anteriorly angled with respect to stem portion 72 from a neutral version as defined by medial/lateral plane 76. For example, as shown in FIG. 13, modular neck portion 80a may be angled approximately 15° anteriorly with respect to medial/lateral plane 76, i.e., central longitudinal axis 79a of modular neck portion 80a defines a 15° angle with plane 76. In another embodiment, modular neck portion 80b may be angled approximately 20° anteriorly with respect to medial/lateral plane 76, i.e., central longitudinal axis 79b of modular neck portion 80b defines a 20° angle with plane 76. In yet another embodiment, modular neck portion 80c may be angled approximately 25° anteriorly with respect to medial/ lateral plane 76, i.e., central longitudinal axis 79c of modular neck portion 80c defines a 25° angle with plane 76. In a modular system, a plurality of neck portions 80 may be provided, wherein the anteversion angle between central longitudinal axis 79 and medial/lateral plane 76 for a given modular neck portion 80 may be from approximately 0° to 25° or more, for example, the anteversion angle may be as small as 13°, 14°, or 16°, and as large as 21°, 23°, or 25°, for example, or any angle therebetween.

Referring to FIG. 14, components of another modular system are shown, wherein neck portion 24 of hip stem 20 is integrally formed therewith, and is shown with a plurality of modular femoral heads 84. In the manner described above, neck portion 24 may be oriented in a desired anteversion alignment, for example, neck portion may be angled approximately 15° anteriorly with respect to stem portion 22 from medial/lateral plane 61, similar to neck portions 24a, 24b, 24c of FIG. 12, i.e., central longitudinal axis 68 of neck portion 24 defines a 15° angle with medial/lateral plane 61. Each modular femoral head 84 includes tapered recess 88 for mating engagement with femoral head fitting 26 of neck portion 24. Each modular femoral head 84 also includes an optional anti-rotation feature, shown as groove 87, for engagement with another anti-rotation feature of neck portion 24, shown as key 85 on femoral head fitting 26, to prevent rotational movement between neck portion 24 and each femoral head 84. Alternatively, each modular femoral head 84 and neck portion 24 may be provided with an oval engagement profile therebetween to provide anti-rotation. As described below, each modular head 84 is itself anteverted with respect to neck portion 24 of hip stem 20.

In particular, the recess 88 of each modular femoral head 84 defines a central axis 86 which is offset from the center of head 84 and from central axis 68 of neck portion 24 such that recess 88 of each head 84 is eccentric with respect to the center of the head 84. Central axis 86 may be angled anteriorly with respect to central longitudinal axis 68 of neck portion 24 such that each modular femoral head 84 is offset from central longitudinal axis 68 upon assembly. For example, modular femoral head 84a may be angled approximately 5° anteriorly with respect to longitudinal axis 68, i.e., central axis 86a of femoral head 84a defines a 5° angle with axis 68. In another embodiment, femoral head 84b may be angled approximately 10° anteriorly with respect to longitudinal axis 68, i.e., central axis 86b of femoral head 84b defines a 10° angle with axis 68. In yet another embodiment, femoral head 84c may be angled approximately 15° anteriorly with respect to longitudinal axis 68, i.e., central axis 86c of femoral head 84c defines a 15° angle with axis 68. In a modular system, a plurality of femoral heads 84 may be provided wherein the angle between central longitudinal axis 68 and axis 86 of same may vary from approximately 1° to 25° or more and, in particular, may be as small as 1°, 3°, 5°, and as large as 21°, 23°, or 25° or more, for example, or any angle therebetween. As discussed above, a larger anteversion angle between the femoral head and the neck portion may provide more optimum anatomical benefits in certain patient, including certain female patients.

Referring to FIG. 15, a view of modular femoral head 84a taken along the line 15-15 in FIG. 14 is shown including central longitudinal axis 68 of neck portion 24 (FIG. 14) and central axis 86a of recess 88 of femoral head 84a. As shown in FIG. 15, axis 86a is offset from, i.e., not coaxial with, axis 68 to provide an offset modular femoral head 84a to achieve an added amount of anteversion alignment of hip stem 20. The offset of axes 86a and 68 provides a larger amount of mass of femoral head 84a on the right side of FIG. 15 as compared to the left side, thereby providing the added anteversion component to enhance the performance of the hip stem. If no offset between femoral head 84 and neck portion 24 was necessary, axis 68 would coincide with central axis 86 of a modular femoral head 84.

As shown in FIGS. 16-17, exemplary components of a modular hip stem system are shown which includes a modular neck portion and a modular femoral head. In FIGS. 16 and 17, the proximal end 78 of modular hip stem 90 is shown which, except as described below, is substantially similar to hip stem 20 (FIGS. 1-5) and hip stem 70 (FIG. 13) described above. The modular hip system shown in FIGS. 16-17 combines the modularity of the systems shown in FIGS. 13 and 14 described above. Hip stem 90 may include modular femoral head 84 having tapered recess 88. Upon assembly, recess 74 of stem portion 72 engages with tapered fitting portion 82 of modular neck portion 80 and recess 88 of modular femoral head 84 engages with femoral head fitting 26 of modular neck portion 80. Modular femoral head 84 includes an optional anti-rotation feature, shown as groove 87, for engagement with another anti-rotation feature of neck portion 80, shown as key 85 on femoral head fitting 26, to prevent rotational movement between neck portion 80 and femoral head 84. Further, neck portion 80 includes a further optional anti-rotation feature, shown as key 81 on tapered fitting portion 82, for engagement with another anti-rotation feature of stem portion 72, shown as groove 83 in recess 74, to prevent rotational movement between neck portion 80 and stem portion 72. Alternatively, each of the foregoing components may be provided with oval engagement profiles therebetween to provide anti-rotation.

Stem portion 72 defines an anatomical medial/lateral plane 91, neck portion 80 defines central longitudinal axis 79, and modular femoral head 84 defines central axis 86. Advantageously, a surgeon may choose any combination of modular components to ensure an adequate degree of anteversion is included in hip stem 90. For example, as shown in FIGS. 16-17, modular femoral head 84 may be angled at an angle α anteriorly with respect to longitudinal axis 79, i.e., central axis 86 of femoral head 84 defines an angle α with axis 79. Also, neck portion 80 may be angled at an angle β anteriorly with respect to medial/lateral plane 76, similar to neck portions 80a, 80b, 80c described above, i.e., central axis 79 of neck portion 80 defines an angle β with axis 76. Angle α may be chosen to be between approximately 1° and 25° or more and, in particular, may be as small as 13°, 14°, or 16°, and as large as 21°, 23°, or 25°, for example, or any angle therebetween. Angle β may be chosen to be between approximately 1° and 25° or more and, in particular, may be as small as 13°, 14°, or 16°, and as large as 21°, 23°, or 25°, for example, or any angle therebetween.

The angle between the neck and the shaft of the femur in certain patients, including many female patients, is typically more varus than the angle between the neck and the shaft of the male femur which is relatively more valgus. Known hip stems are not shaped with a sufficiently varus neck/shaft angle which would provide optimum results in certain female patients. Also, in order to accommodate a hip stem having a more varus neck/shaft angle without the need to lengthen leg length, it is typically necessary to osteotomize a greater portion of the metaphysis of the femur in female patients than in male patients. Specifically, in certain females, the femur is osteotomized at a location near the lesser trochanter. This results in less of the metaphysis being available for hip stem fixation in many female patients as compared to male patients, thereby increasing the importance of diaphyseal fixation of the hip stem in female patients.

Figure 18:
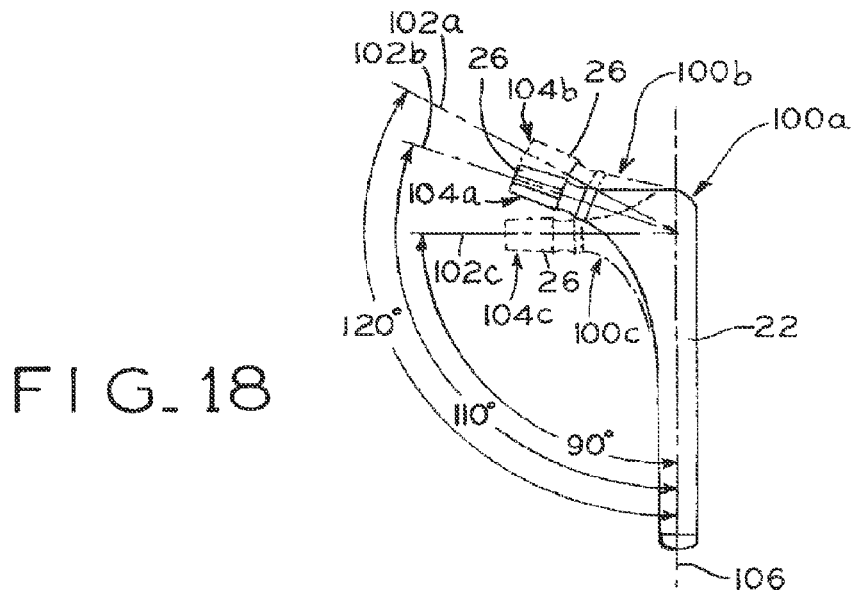
FIG. 18 is an anterior/posterior schematic view of several hip stems each having an integral stem portion and neck portion and showing a range of possible neck/shaft angles for the neck portions.

Referring to FIG. 18, several embodiments of hip stem 100 are shown which, except as described below, are substantially similar to hip stem 20 (FIGS. 1-5), described above. Each hip stem 100 includes integral stem portion 22 and neck portion 104. Hip stem 100 defines central longitudinal axis 106 extending through stem portion 22 and includes a neck portion 104 having a central longitudinal axis 102. Central longitudinal axis 106 and each central longitudinal axis 102 define an angle therebetween which may be chosen depending on the anatomy of the patient. For example, neck portion 104a, shown in solid lines in FIG. 18, may have central longitudinal axis 102a which defines an angle of approximately 110° with axis 106. If more valgus neck/shaft angle is desired, a surgeon may choose hip stem 100b, shown in dashed lines in FIG. 18, including neck portion 104b having central longitudinal axis 102b which defines an angle of approximately 120° with axis 106. Alternatively, if less valgus (more varus) neck/shaft angle is desired, a surgeon may choose hip stem 100c, shown in dashed lines in FIG. 18, including neck portion 104c having central longitudinal axis 102c which defines an angle of approximately 90° with axis 106. In a system of hip stems 100 having various neck/shaft angles, a particular hip stem may be selected having a neck/shaft angle corresponding to the anatomy of a particular patient. In this system, the neck/shaft angle may range from approximately 90° to approximately 145°, and in particular, may be as small as 90°, 110°, or 120° or any increments therebetween, for example. Advantageously, hip stem 100 may be chosen to have more varus orientation without increasing the leg length of the hip implant system. Hip stem 100 may allow a surgeon to select from a sufficient variation of hip stems having various neck/shaft angles to optimize results in certain female patients.

Figure 19:
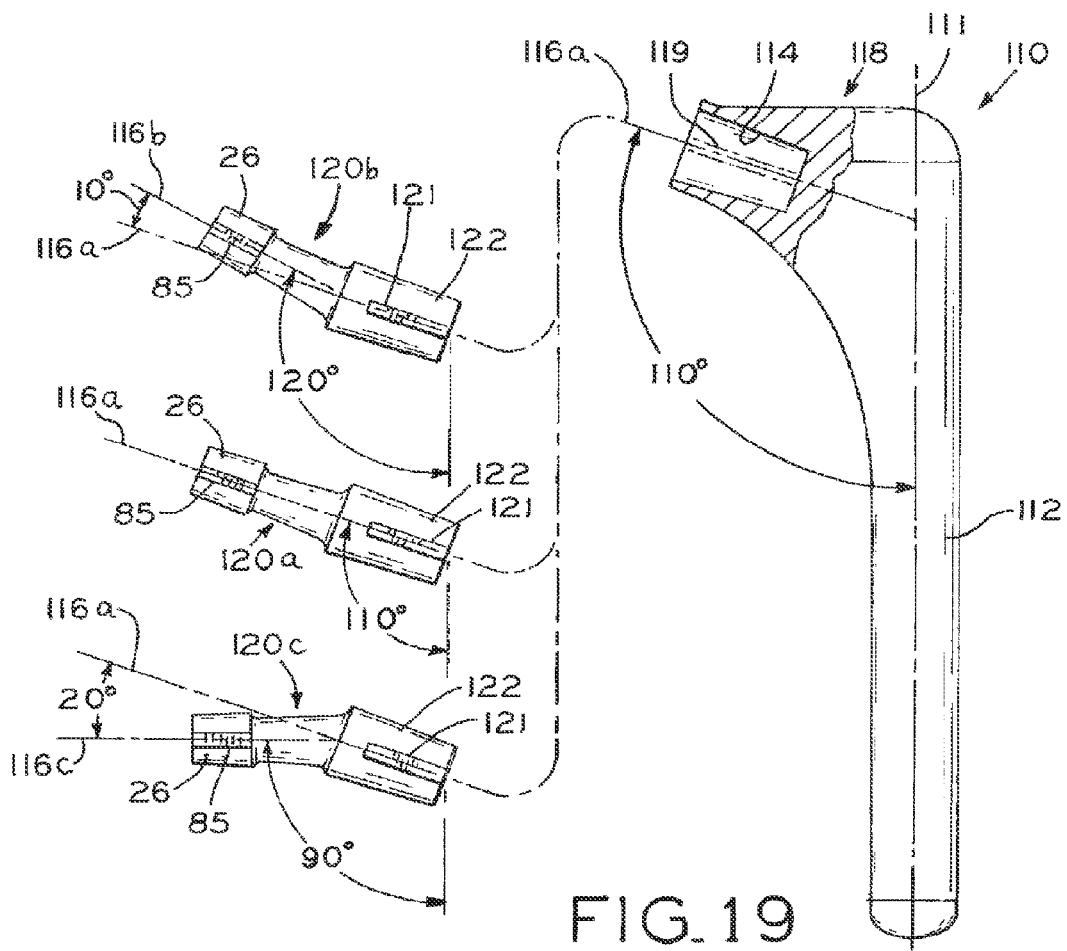
FIG. 19 is a partially sectioned anterior/posterior view of components of a modular hip stem system including a hip stem portion and a plurality of modular neck components having various neck/shaft angles which may be used with the modular hip stem portion.

Referring to FIG. 19, a modular hip stem system includes hip stem 110 which, except as described below, is substantially similar to hip stem 20 (FIGS. 1-5), described above. Hip stem 110 may include stem portion 112 and a plurality of modular neck portions 120 each having tapered fitting portion 122 for mating engagement in tapered recess 114 in proximal end 118 of stem portion 112 and femoral head fitting 26 for acceptance of a modular femoral head. Each neck portion 120 includes an optional anti-rotation feature, shown as key 121 on tapered fitting portion 122, for engagement with another anti-rotation feature of stem portion 112, shown as groove 119 in recess 114, to prevent rotational movement between each neck portion 120 and stem portion 112. Alternatively, each neck portion 120 and stem portion 112 may be provided with oval engagement profiles to provide anti-rotation. Each modular neck portion 120 defines a central longitudinal axis 116 forming an angle with central longitudinal axis 111 of stem portion 112. In one embodiment, modular neck portion 120a may have central longitudinal axis 116a which forms an angle of approximately 110° with axis 111.

If a surgeon desires a larger neck/shaft angle, modular neck portion 120b may be chosen which defines central longitudinal axis 116b which forms an angle of approximately 120° with axis 111 and an angle of approximately 10° with central longitudinal axis 116a, i.e., a +10° change in neck/shaft angle from modular neck portion 120a. If a surgeon desires a smaller neck/shaft angle, modular neck portion 120c may be chosen which defines central longitudinal axis 116c which forms an angle of approximately 90° with axis 111 and an angle of approximately 20° with central longitudinal axis 116a, i.e., a −20° change in neck/shaft angle from modular neck portion 120a. Various values for the neck/shaft angle may be chosen depending on the varus/valgus anatomy of a particular patient. For example, the neck/shaft angle may range from approximately 90° to approximately 145°, and in particular, may be 90°, 110°, or 120°, or any increment therebetween. Hip stem 110 advantageously allows a surgeon to select from a variety of modular neck portions to vary the neck/shaft angle to optimize results in certain female patients.

The present inventors have also observed that as certain patients age, particularly females, the cortex of bone in the metaphysis and in the diaphysis of the proximal femur typically becomes thinner, particularly from the level of the lesser trochanter downwardly. The thinning cortex of the metaphysis and diaphysis results in a "stovepipe" shape of the cortex in the metaphysis and a pronounced widening of the intramedullary canal in the diaphysis, respectively. These effects are more pronounced with women who have osteoporosis, which results in further thinning of the cortex and consequent widening of the intramedullary canal, and in particular, a reduction of bone stock in the proximal diaphysis.

When cementless prostheses are used, the widened intramedullary canal of certain patients, particularly aging females, promotes a tendency for using a wider hip stem to more completely fill the intramedullary canal and achieve initial fixation. In many existing hip stems, stiffness increases with increasing width, such that use of wider hip stems of increased stiffness could result in stress shielding around the hip stem. Advantageously, the hip stems described herein which include a core, a polymer matrix intermediate layer, and porous metal outer layer, have a stiffness modulus which more closely approximates the stiffness modulus of cortical bone. This allows relative motion between the hip stem and the femur to be minimized, and allows more loading to be distributed to the cortical bone to reduce the potential for stress shielding as opposed to known, more stiff hip stems which have only a core and a porous metal coating.

Additionally, the inventors have observed that in females, the intramedullary canal tends to widen relatively more in the anterior/posterior plane, as viewed with a lateral x-ray, for example, than in the medial/lateral plane, particularly in females with osteoporosis, which commonly causes thinning of the posterior cortex of the diaphysis. Thus, when the anterior/posterior and medial/lateral diameters of the intramedullary canal are typically not equal, known hip stems which have a substantially cylindrical shape may not achieve optimal fixation in the diaphysis.

Figure 20:
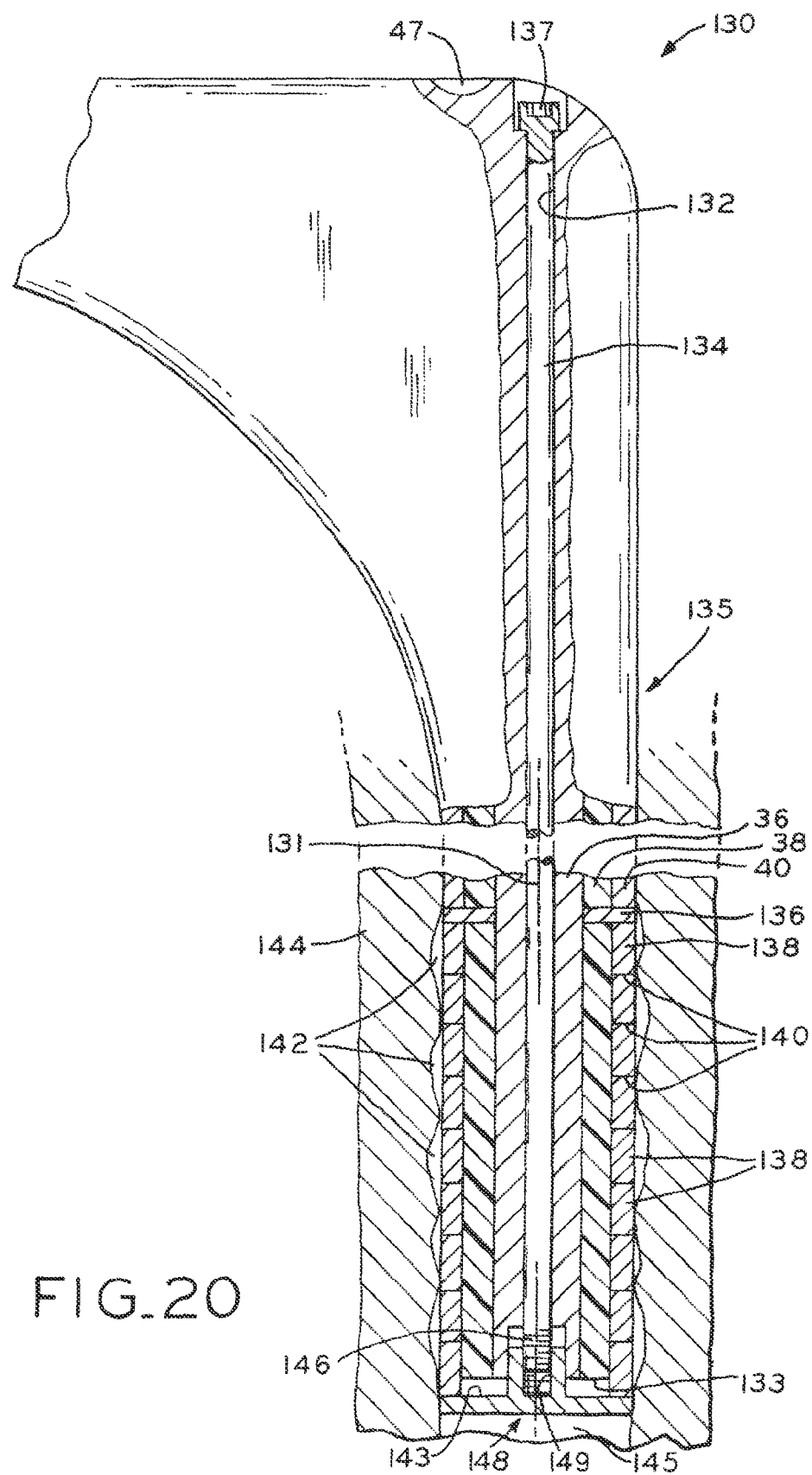
FIG. 20 is a cross-sectional view of a portion of a hip stem within the diaphysis of a femur, further illustrating an embodiment of a distal end fixation mechanism in a non-expanded condition.

Referring to FIG. 20, a portion of hip stem 130 is shown which, except as described below, is substantially similar to hip stem 20 shown in FIGS. 1-5 and described above. Hip stem 130 may include stem portion 135 with core 36, polymer matrix layer 38, and porous metal layer 40. Stem portion 135 may further include a distal end fixation mechanism operable between a first, non-expanded condition and a second, expanded condition. The distal end fixation mechanism may include a plurality of expansion points 140 in porous metal layer 40, such as slits, hinges, or weakened areas, for example, which define a plurality of radially expandable portions 138. The distal end fixation mechanism may also include activation member 148 having a threaded aperture 149 for mating engagement with threaded end 146 of shaft 134. Shaft 134 may be a permanent part of hip stem 130 and may be rotatably positioned within throughbore 132 in core 36. Shaft 134 includes proximal end 137 having suitable instrument engagement structure, such as a hex fitting, for example, for engagement with an actuator device 139 (FIG. 21) for imparting rotational motion to shaft 134.

In operation and referring to FIG. 21, after hip stem 130 is initially implanted in intramedullary canal 145 of the prepared femur 144, shaft 134 may be rotated by actuator device 39 in the general direction of Arrow A to thread threaded end 146 of shaft 134 into threaded aperture 149 of activation member 148. Rotation of shaft 134, and the threading of end 146 thereof into threaded aperture 149 of activation member 148, causes movement of activation member 148 towards distal end 133 of hip stem 130 in the general direction of Arrow B towards distal end 133 of hip stem 130. Movement of activation member 148 along the direction of Arrow B causes activation member 148 to compress expandable portions 138 of porous metal layer 40 against a fixed reaction surface provided by abutting portion 136 of core 36, thereby causing expansion points 140 in porous metal layer 40 to deform and expand radially expandable portions 138 from a first, non-expanded condition to a second, expanded condition. The plurality of radially expandable portions 138 cause hip stem 130 to widen and substantially fill intramedullary canal gaps 142 (FIG. 20), thereby enhancing distal fixation of hip stem 130 in the diaphysis of femur 144.

The degree of expansion of expandable portions 138 may be controlled by the amount of rotation of shaft 134. For example, in one embodiment, a half turn, or 180° turn, of shaft 134 with the actuator device provides a limited degree of expansion of expandable portions 138 to provide initial fixation if the intramedullary canal of femur 144 is only slightly wider than hip stem 130. In one embodiment, two complete turns, or a 720° turn, of shaft 134 provides maximum expansion of expandable portions 138 to provide initial fixation if the intramedullary canal of femur 144 is substantially wider than hip stem 130, wherein shaft 134 is rotated until surface 143 of activation member 148 abuts distal end 133 of hip stem 130 to limit the travel of activation member 148. In this manner, the amount of rotation imparted to shaft 134 may advantageously allow the surgeon to provide the appropriate amount of expansion of expandable portions 138 to ensure adequate diaphyseal fixation of hip stem 130, which may be verified by X-ray or other imaging. In one embodiment, expansion points 140 may include a sliding-enhancement element, for example, a plastic sheet, to facilitate movement of porous metal layer 40 radially outward instead of a potential collapse of porous metal layer 40 in the direction of Arrow B with no radial expansion. Advantageously, portions 138 in the first, non-expanded condition define the original cross-sectional shape of the hip stem. After implantation, deformation of portions 138 advantageously allows the hip stem to have a larger cross-sectional shape in the distal portion thereof to enhance diaphyseal fixation of the hip stem in the femur.

Referring to FIGS. 22-23, a portion of hip stem 150 is shown which, except as described below, is substantially similar to hip stem 20, shown in FIGS. 1-5, and hip stem 130, shown in FIGS. 20-21. Hip stem 150 may include a distal end fixation mechanism having expandable structure 155 which facilitates widening of hip stem 150 near distal end 152 to enhance distal fixation of hip stem 150 in the diaphysis of femur 144. Core 36 may be provided with central throughbore 154. Core 36, polymer matrix layer 38 and porous metal layer 40 may include a plurality of passages 153 providing for travel of a filler material within throughbore 154 into expandable structure 155. Although illustrated as horizontally oriented, passages 153 may be oriented diagonally or any other orientation to facilitate flow of the filler material into expandable structure 155 from throughbore 154. Any number of passages 153 may be provided and the width of passages 153 may be varied to regulate the flow of filler material 156 (FIG. 23) into expandable structure 155. As shown in FIG. 22, prior to expansion within intramedullary canal 145 of femur 144, expandable structure 155 remains substantially flat and non-expanded and does not significantly increase the overall diameter of hip stem 150. Alternatively, expandable structure 155 may be disposed within a recessed area of porous metal coating 40 of hip stem 150 such that expandable structure 155 does not increase the overall diameter of hip stem 150.

As shown in FIG. 23, upon introduction of filler material 156, e.g., bone cement or polymethylmethacrylate (PMMA), into throughbore 154 by a tube or other suitable delivery device in the general direction of Arrow C, filler material 156 migrates into passages 153 and fills expandable structure 155. Expansion of expandable structure 155 widens distal end 152 of hip stem 150 to substantially fill any gaps 142 between hip stem 150 and the intramedullary canal of femur 144. The filler supply device is gradually proximally removed from central throughbore 154 while simultaneously distally filling central throughbore 154 and, consequently, passages 153 and expandable structure 155 to ensure complete filling of expandable structure 155 to the desired expansion state. Expandable structure 155 may be formed of any suitable biocompatible material, such as the materials used for the prosthetic implant described in U.S. patent application Ser. No. 11/250,927, filed Oct. 14, 2005, titled METHOD AND APPARATUS FOR REDUCING FEMORAL FRACTURES, assigned to the assignee of the present application, the disclosure of which is hereby expressly incorporated herein by reference.

In some embodiments, expandable structure 155 may be expanded non-uniformly around the circumference of hip stem 150, for example, by varying the number, relative locations, and relative cross sections of passages 153 in hip stem 150. This may allow hip stem 150 to more optimally achieve fixation in the diaphysis because hip stem 150 may expand further in the anterior/posterior plane than in the medial/lateral plane, for example, to provide optimal fixation in females with osteoporosis wherein the width of the anterior/posterior plane of the intramedullary canal may exceed that in the medial/lateral plane. As discussed above, osteoporosis in females commonly causes thinning of the posterior cortex of the diaphysis. The ability to expand in a non-uniform manner, particularly expanding further posteriorly than either medially, laterally, or anteriorly, allows hip stem 150 to achieve optimum fixation.

In a total hip arthroplasty, a prosthetic acetabular cup component is seated within a patient's acetabulum anteriorly of the medial wall of the pelvis. In certain patients, loading from the femoral prosthesis may be transmitted to the pelvis primarily around the rim of the acetabular cup, as opposed to being distributed more evenly around the hemispherical portion of the acetabular cup, which could potentially result in stress shielding around the hemispherical portion of the acetabular cup. Stress shielding of bone around the hemispherical portion of the acetabulum may cause resorption of bone in the medial wall of the pelvis posteriorly of the acetabulum, potentially resulting in migration of the acetabular cup into the medial wall of the pelvis. The present inventors have observed that in female patients, the medial wall of the pelvis is often thinner than in most men.

Figure 24:
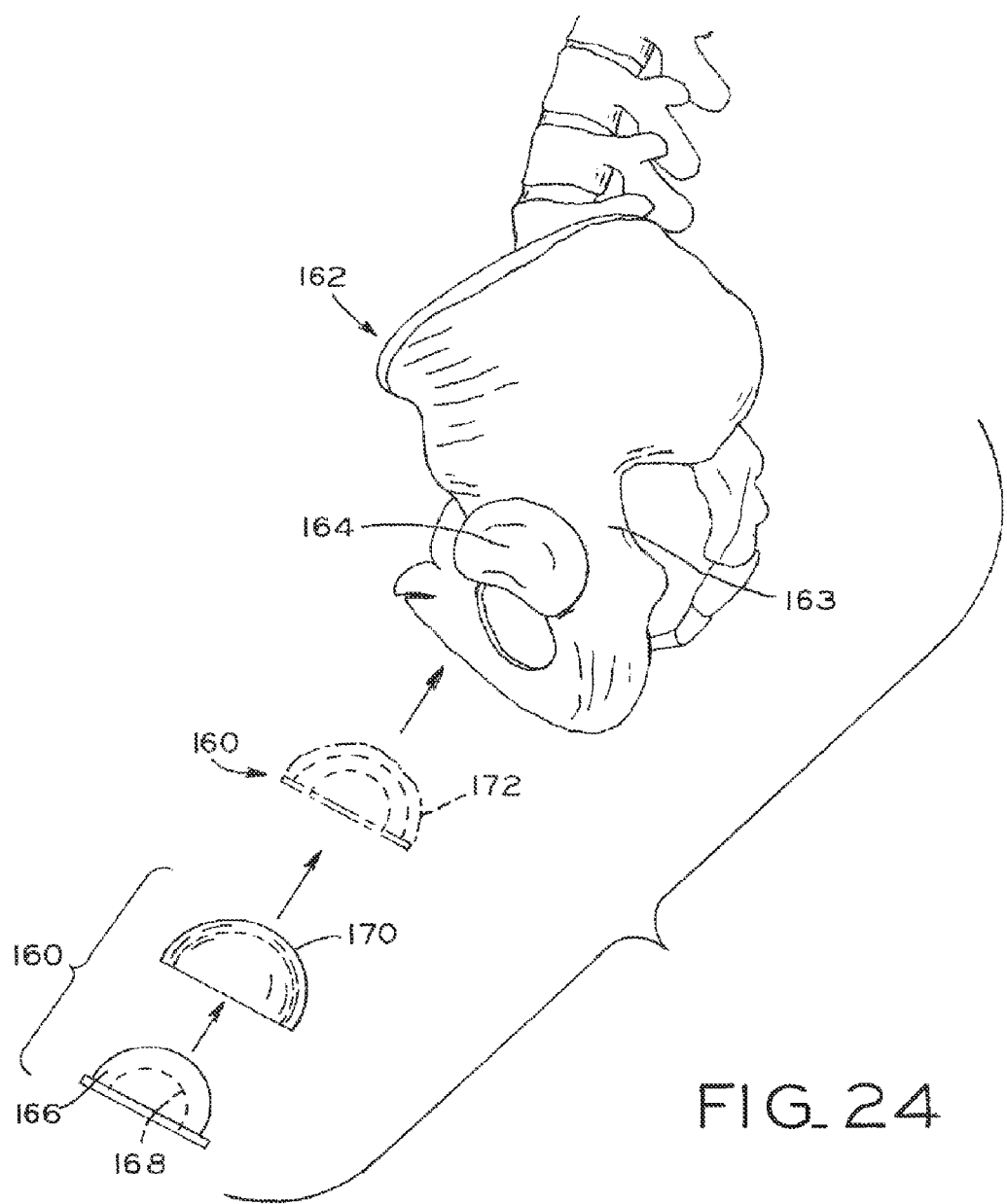
FIG. 24 is an exploded view of a flexible acetabular cup and liner, and a pelvic region of a patient's anatomy.

Referring to FIG. 24, a flexible acetabular cup 160 is shown, which generally includes a liner 166 made of ultra high molecular weight polyethylene, for example, including a hemispherical articulating surface 168. Liner 166 is fitted within a porous metal cup portion 170 which may be made from a metal wire mesh of titanium fibers, a metal bead matrix, or may be a porous metal layer produced in accordance with Trabecular Metal™ technology available from Zimmer, Inc. of Warsaw, Ind. Cup portion 170 may be formed relatively thin, or may include relief slits therein such that cup portion 170 is generally flexible, as represented by dashed lines 172 in FIG. 24, to more evenly distribute acetabular loading around both the rim and the hemispherical portions of cup portion 170 to reduce the potential for stress shielding and, in turn, to reduce the potential for migration of acetabular cup 160 into the medial wall 163 of the pelvis 162.

Referring to FIG. 25, acetabular cup 180 according to another embodiment is shown, which generally includes liner 182 made of ultra high molecular weight polyethylene, for example, intermediate layer 184 of a polymer matrix similar to that of hip stem 20 described above, which may be formed of an inert polyaryletherketone ("PAEK") polymer such as for example, polyetheretherketone ("PEEK"), and porous metal layer 186 which may be made from a metal wire mesh of titanium fibers, a metal bead matrix, or may be a porous metal layer produced in accordance with Trabecular Metal™ technology available from Zimmer, Inc. of Warsaw, Ind., for example. Liner 182 includes a hemispherical bearing surface 188 for articulating receipt of the femoral head component of a hip stem, such as the various hip stems described herein. Porous metal layer 186 allows osseointegration of acetabular cup 180 into the surrounding bone of the acetabulum. Advantageously, polymer matrix layer 184 allows flexing movement between liner 182 and porous metal layer 186 to provide a stiffness for acetabular cup 180 which more closely approximates that of bone than the stiffness of known acetabular cups. In this manner, loads from the femoral head component of the hip stem are distributed more evenly about the hemispherical portion of the cup to the surrounding bone of the acetabulum, thereby reducing the potential for stress shielding and resulting migration of the cup into the medial wall of the pelvis.

Referring to FIG. 26, acetabular cup 190 according to a further embodiment is shown which generally includes liner 192 made of ultra high molecular weight polyethylene, for example, and porous metal layer 194 which may be a metal wire mesh of titanium fibers, or alternatively, may be a metal bead matrix or other porous metal structure produced in accordance with Trabecular Metal™ technology available from Zimmer, Inc. of Warsaw, Ind., for example. Liner 192 includes a hemispherical bearing surface 196 for articulating receipt of the femoral head component of a hip stem, such as the various hip stems described herein. Porous metal layer 194 allows osseointegration of acetabular cup 190 into the surrounding bone of the acetabulum, and advantageously, further includes a loading rib 198 disposed around the outer hemispherical portion of porous metal layer 194 which contacts the surrounding bone of the acetabulum to transfer loads thereto, such that loads from the femoral head component of the hip stem are distributed more evenly about the hemispherical portion of the cup to the surrounding bone of the acetabulum, thereby reducing the potential for stress shielding and resulting migration of the cup into the medial wall of the pelvis.

Figure 27:
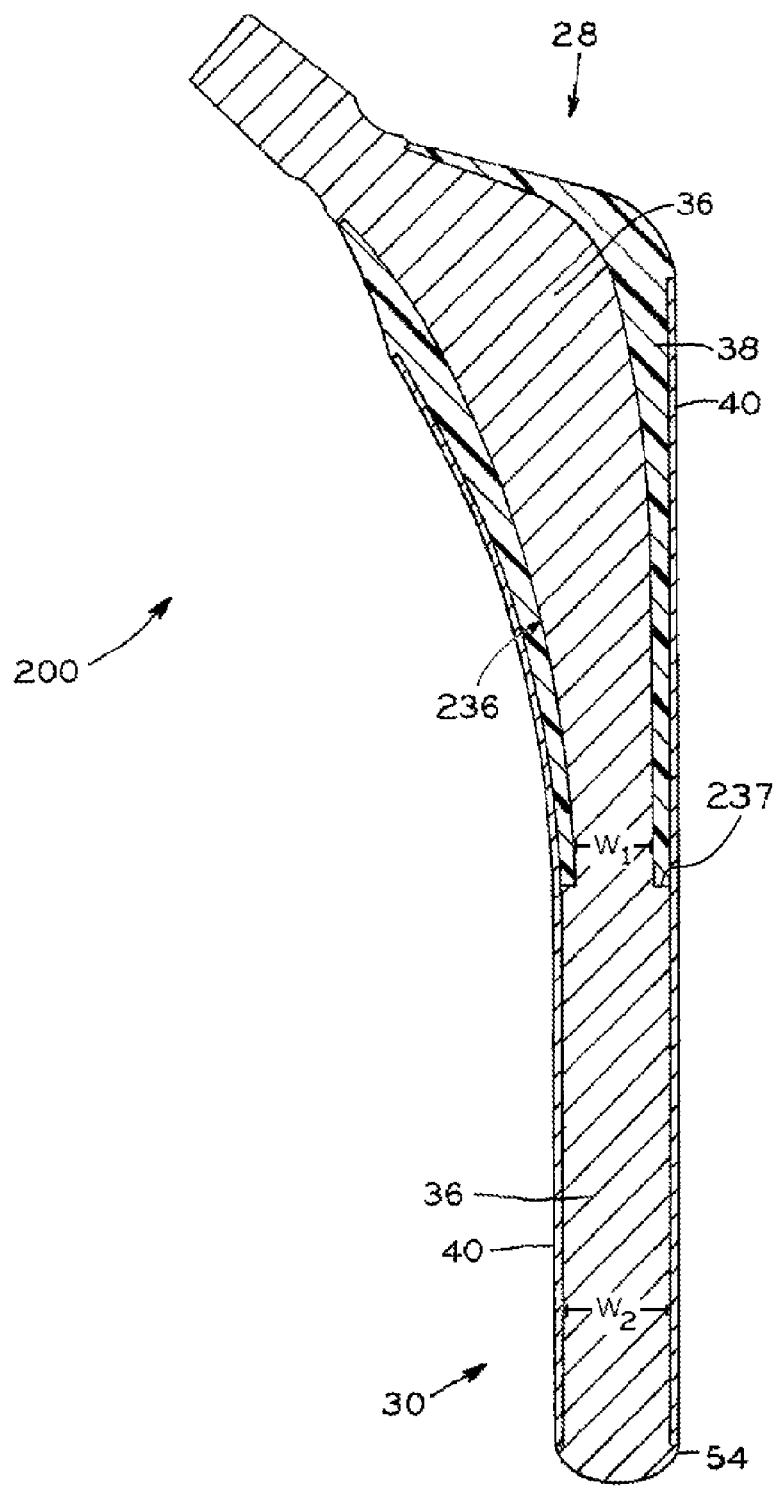
FIG. 27 is a sectional view of a hip stem according to a further embodiment.

Referring to FIG. 27, hip stem 200 according to a further embodiment of the present invention is shown which, except as described below, is similar to hip stem 20 shown in FIGS. 1-5 and described above. Hip stem 20 generally includes proximal end 28 and distal end 30, wherein proximal end 28 is configured similarly to that of hip stem 20 in that proximal end 28 of hip stem 200 includes core 36, polymer matrix layer 38, and porous metal layer 40 as described above with respect to hip stem 20. However, distal end 30 of hip stem 200 includes only core 36 and porous metal layer 40, and lacks polymer matrix layer 38. In this manner, distal end 30 of hip stem 200 has a higher stiffness than proximal end 28 of hip stem 200 to facilitate initial fixation of distal end 30 of hip stem 200 in the diaphysis of the femur, wherein proximal end 28 of hip stem 200 has a stiffness which more closely mimics that of natural bone than known hip stems to thereby transfer loading to the surrounding bone of the metaphysis around proximal end 28 of hip stem 200 to reduce the potential for stress shielding. A proximal width $W_1$ of core 36 measured near proximal end 28 and a distal width $W_2$ of core 36 measured near distal end 30 are labeled in FIG. 27, with proximal width $W_1$ being smaller or narrower than distal width $W_2$. Near proximal end 28, core 36 defines cavity 236 that receives polymer matrix layer 38, as shown in FIG. 27. Core 36 also includes a proximally facing shoulder 237 between proximal end 28 and distal end 30, with polymer matrix layer 38 terminating at shoulder 237. As discussed above, in certain patients, such as in certain female patients, not only does the cortex of the metaphysis thin, but a greater extent of the metaphysis of the femur must be osteotomized during a total hip arthroplasty, which results in less of the remaining metaphysis being available for fixation. Thus, for these types of procedures, hip stem 200 advantageously includes a relatively stiff distal end 30 for enhanced initial fixation in the diaphysis of the femur, and a relatively more flexible proximal end 28 to prevent stress shielding and bone resorption in the metaphysis of the femur.

Figure 28:
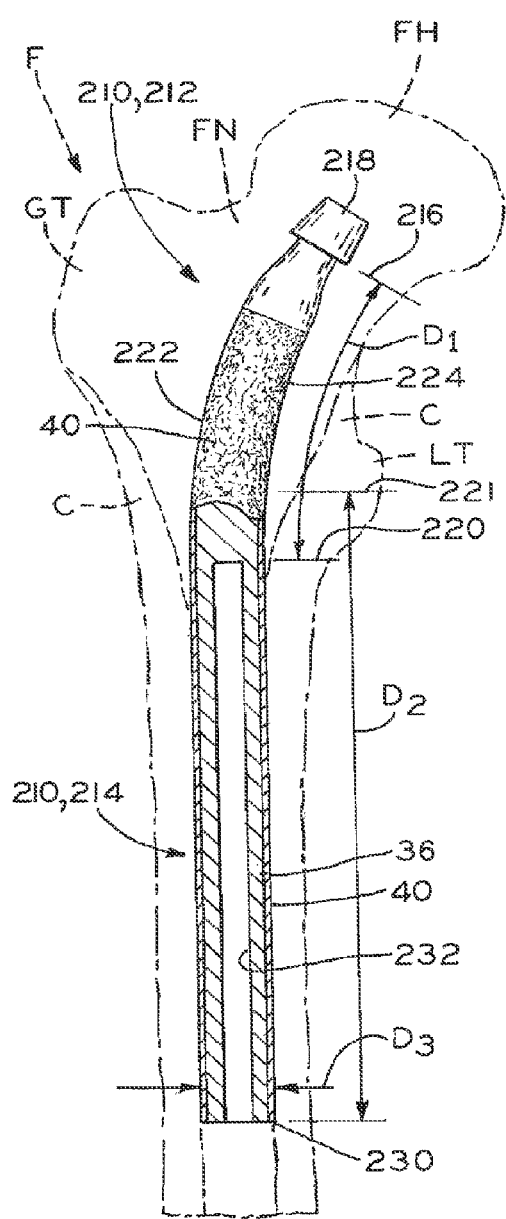
FIG. 28 is an anterior/posterior view of a hip stem according to a further embodiment, showing portions of the posterior femur in phantom.
Figure 29:
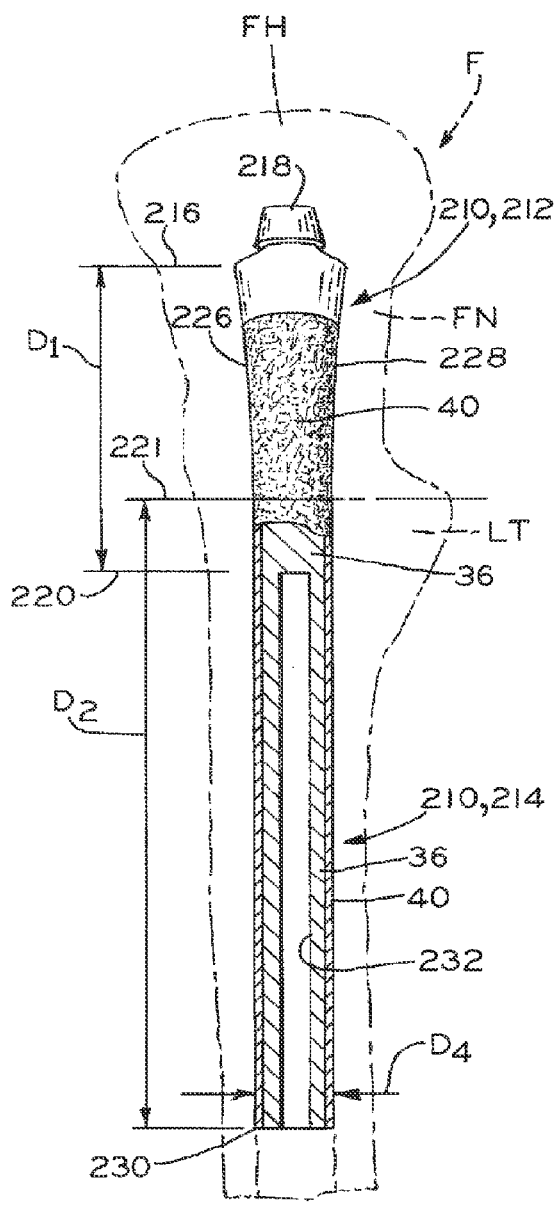
FIG. 29 is a medial/lateral view of the hip stem of FIG. 28, showing portions of the posterior femur in phantom.

Referring to FIGS. 28 and 29, anterior and lateral views of a hip stem 210 according to a further embodiment are shown, respectively. In FIGS. 28 and 29, hip stem 210 is shown superimposed on proximal femur "F", shown in ghost lines, to illustrate features of hip stem 210 in relation to the proximal femur. Hip stem 210 is particularly useful in patients, such as older female patients, for example, whose proximal femur is characterized by thinned cortices "C" in the metaphysis and diaphysis as shown in FIG. 28, perhaps with complete loss of the medial and posterior cortices in the metaphysis resulting in the "stovepipe" shape of the intramedullary canal seen in FIG. 28, as well as a thinned intramedullary canal in the diaphysis. Although anatomical features of the proximal femur, including the greater trochanter "GT", lesser trochanter "LT", femoral neck "FN", and femoral head "FH" are shown in ghost lines in FIGS. 28 and 29 in order to illustrate features of hip stem 210 in relation thereto, it is to be understood that the femoral neck and head, as well as portions of the greater trochanter, are osteotomized during a total hip arthroplasty to accommodate insertion of femoral stem 210 into the prepared intramedullary canal of the femur.

Hip stem 210 generally includes a proximal, or metaphyseal, portion 212 and a distal, or diaphyseal, portion 214. Hip stem 210 may be constructed in a similar manner as hip stem 20 described above with respect to FIGS. 1-5, wherein hip stem 210 may include a core 36, a polymer matrix layer (not shown) disposed over at least a portion of core 36, and a porous metal layer 40, such as those described above or a grit-blasted layer, disposed over the polymer matrix layer. Proximal portion 212 of stem 210 has a length dimension $D_1$ measured from stage line 216, which is typically 15 mm from the top of the lesser trochanter, to line 220 at the base of the lesser trochanter which may be as small as 30 mm or 35 mm to as large as 40 mm or 45 mm for example, or any length therebetween. As may be seen from FIG. 28, proximal portion 212 of stem 210 is not trapezoidally shaped as are many known hip stems when viewed in the anterior/posterior view of FIG. 28, but rather has a "goose neck" profile, including medially curved, complementary radiused lateral and medial sides 222 and 224. In particular, lateral side 222 is curved medially in order to clear the greater trochanter and prevent loading on any portion of the greater trochanter which remains after the osteotomy. When viewed in the lateral view of FIG. 29, proximal portion 212 of hip stem 210 has a flared shape including anterior and posterior sides 226 and 228 which flare slightly outwardly, such as between 1 and 2 mm, for example, in the anterior and posterior directions as same approach the proximal end of hip stem 210.

The neck portion and the femoral head (not shown) of proximal portion 212 of hip stem 210 may be integrally formed with hip stem 210 and may be aligned in desired anteversion/retroversion and varus/valgus angles in the same manner as the other hip stems described above with reference to FIGS. 12 and 18. Alternatively, the neck portion and the femoral head of hip stem 210 may be configured as one or more modular components to provide the desired anteversion/retroversion and varus/valgus angles in the manner described above with reference to FIGS. 13-17 and 19.

Distal portion 214 of hip stem 210 may have a circular or trapezoidal cross section, and is elongated with respect to known hip stems to allow the distal portion 214 to engage the cortex of the diaphyseal isthmus, having a length dimension $D_2$ measured from the from the mid lesser trochanter line 221 to the distal end 230 of the hip stem 210 which may be as small as 100 mm, 105 mm, or 110 mm and as large as 125 mm, 130 mm, or 135 mm, for example, or any length therebetween. Near the distal end 230, the width of hip stem 210 at dimension $D_3$ measured laterally-medially may vary from 10 mm to 18 mm and, as shown in FIG. 29, the width of hip stem 210 at dimension $D_4$ measured anteriorly-posteriorly may be 1 mm or more greater than dimension $D_3$, i.e., may vary between 11 mm and 19 mm, in order to optimally fit within the intramedullary canal of certain patients, particularly in older female patients, wherein the intramedullary canal is slightly wider in the anterior/posterior dimension and in the medial/lateral dimension.

Additionally, distal portion 214 of hip stem 210 may have a substantially hollow construction, including an elongated blind cavity 232 extending inwardly from distal end 230 toward proximal portion 212 of hip stem 210, optionally extending to line 220 at the base of the lesser trochanter. Cavity 232 allows distal portion 214 of hip stem 210 to flex, such that the stiffness modulus of distal portion 214 of hip stem 210 more closely approximates the stiffness modulus of the femoral bone surrounding hip stem 210 to aid in prevention of stress shielding around distal portion 214 of hip stem 210. Alternatively, distal portion 214 of hip stem 210 may be formed to include a core/polymer matrix/porous outer layer construction similar to the other hip stems disclosed herein to provide a stiffness modulus which more closely approximates the stiffness modulus of the femoral bone around distal portion 214 of hip stem 210. In a still further embodiment, distal portion 214 of hip stem 210 may include a plurality of grooves, slopes, or other enervations or weakenings therein to reduce the stiffness modulus thereof.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A prosthetic hip stem comprising:
    a core having a proximal region and a distal region;
    a porous metal layer substantially covering the proximal region of the core and the distal region of the core; and
    an intermediate polymer matrix layer located between the proximal region of the core and the porous metal layer, the polymer matrix layer terminating before reaching the distal region of the core such that the prosthetic hip stem lacks the polymer matrix layer between the distal region of the core and the porous metal layer.

2. The prosthetic hip stem of claim 1, wherein at least a portion of the proximal region of the core is narrower than the distal region of the core to define a cavity for receiving the polymer matrix layer.

3. The prosthetic hip stem of claim 1, wherein the distal region of the core includes a proximally facing shoulder along an interface with the proximal region of the core, the polymer matrix layer terminating at the shoulder.

4. The prosthetic hip stem of claim 1, wherein the polymer matrix layer extends from the proximal region of the core to define a proximal outer surface of the polymer matrix layer and the distal region of the core defines a distal outer surface of the core, the proximal outer surface of the polymer matrix layer being substantially flush with the distal outer surface of the core in an area where the proximal region of the core borders the distal region of the core.

5. The prosthetic hip stem of claim 1, wherein the distal region of the core includes a boss that projects outwardly from a distal-most end of the prosthetic hip stem, the boss supporting the porous metal layer that covers the distal region of the core.

6. The prosthetic hip stem of claim 5, wherein the porous metal layer terminates before reaching the boss at the distal-most end of the prosthetic hip stem.

7. The prosthetic hip stem of claim 1, wherein the core comprises at least one of a cobalt-chromium-molybdenum alloy and a titanium alloy.

8. The prosthetic hip stem of claim 1, wherein the polymer matrix layer comprises a polyaryletherketone polymer.

9. The prosthetic hip stem of claim 1, wherein the porous metal layer comprises at least one of a metal wire mesh and a metal bead matrix.

10. A prosthetic hip stem comprising:
    a proximal region including a proximal core, a proximal polymer matrix layer coupled to the proximal core, and a proximal porous metal layer coupled to the proximal polymer matrix layer such that the proximal polymer matrix layer is located between the proximal core and the proximal porous metal layer; and
    a distal region including a distal core and a distal porous metal layer coupled directly to the distal core.

11. The prosthetic hip stem of claim 10, wherein the proximal polymer matrix layer terminates before reaching the distal region.

12. The prosthetic hip stem of claim 10, wherein the proximal region is more flexible than the distal region.

13. The prosthetic hip stem of claim 10, wherein the coupling between the distal porous metal layer and the distal core is more rigid than the coupling between the proximal porous metal layer and the proximal core.

14. The prosthetic hip stem of claim 10, wherein at least a portion of the proximal core is narrower than the distal core to define a cavity for receiving the proximal polymer matrix layer.

15. The prosthetic hip stem of claim 10, wherein the distal core includes a proximally facing shoulder along an interface with the proximal core, the proximal polymer matrix layer terminating at the shoulder.

16. The prosthetic hip stem of claim 10, wherein the proximal polymer matrix layer defines a proximal outer surface of the proximal polymer matrix layer and the distal core defines a distal outer surface of the distal core, the proximal outer surface of the proximal polymer matrix layer being substantially flush with the distal outer surface of the distal core in an area where the proximal core borders the distal core.

17. The prosthetic hip stem of claim 10, wherein the proximal porous metal layer defines a proximal outer surface and the distal porous metal layer defines a distal outer surface, the proximal outer surface being substantially flush with the distal outer surface in an area where the proximal core borders the distal core.

18. A prosthetic hip stem comprising:

a core having a proximal region and a distal region;

a porous metal layer substantially covering the proximal region of the core and the distal region of the core; and an intermediate polymer matrix layer extending between the proximal region of the core and the porous metal layer without extending between the distal region of the core and the porous metal layer such that the porous metal layer is more flexibly coupled to the proximal region of the core than to the distal region of the core.

19. The prosthetic hip stem of claim 18, wherein the porous metal layer is directly coupled to the distal region of the core.

20. The prosthetic hip stem of claim 18, wherein a proximal portion of the porous metal layer is received in a proximal recess defined by the polymer matrix layer.

21. The prosthetic hip stem of claim 18, wherein a distal portion of the porous metal layer is received in a distal recess defined by the distal region of the core.

* * * * *